US008318657B2

(12) United States Patent
Saccone et al.

(10) Patent No.: US 8,318,657 B2
(45) Date of Patent: Nov. 27, 2012

(54) METHODS AND COMPOSITIONS FOR PREVENTING AND/OR TREATING PANCREATITIS

(75) Inventors: Gino Tony Patrick Saccone, Glandore (AU); James Toouli, Hove (AU); Colin Carati, Brighton (AU); Mayank Bhandari, Mitchell Park (AU); Mark Brooke-Smith, Leabrook (AU)

(73) Assignee: Flinders Technologies Pty Ltd. (AU)

( * ) Notice: Subject to any disclaimer, the term of this patent is extended or adjusted under 35 U.S.C. 154(b) by 706 days.

(21) Appl. No.: 12/095,375

(22) PCT Filed: Dec. 1, 2006

(86) PCT No.: PCT/AU2006/001813
§ 371 (c)(1),
(2), (4) Date: Oct. 22, 2008

(87) PCT Pub. No.: WO2007/062469
PCT Pub. Date: Jun. 7, 2007

(65) Prior Publication Data
US 2009/0081186 A1    Mar. 26, 2009

(30) Foreign Application Priority Data

Dec. 1, 2005  (AU) ................................ 2005906722

(51) Int. Cl.
*C07K 14/00* (2006.01)
(52) U.S. Cl. ........................................... 514/1; 530/350
(58) Field of Classification Search ....... 514/1; 530/350
See application file for complete search history.

(56) References Cited

FOREIGN PATENT DOCUMENTS
WO    WO 2004/065560 A    8/2004
WO    WO 2005/014849 A    2/2005

OTHER PUBLICATIONS www.possumcentre.com.au/Pages/Bushtail.html, 2012.*
Gregersen et al. 1993. Blockade of galanin-induced inhibition of insulin secretion from isolated mouse islets by the non-methionine containing antagonist M35. European Journal of Pharmacology. 232(1): 35-39, Abstract only provided.*
Brooke-Smith, M., et al., "Galanin is located in nerves associated with the pancreatic vasculature and reduces pancreatic vascular perfusion," *Gastroenterology*, vol. 126(4), Suppl. 2, p. A526 (2004).
Zhao, Y-Q, et al., "Protective effects of rhubarb on experimental severe acute pancreatitis," *World J. Gastroenterol.*, vol. 10(7), pp. 1005-1009 (2004).
Ahern, Bo et al.; "Galanin and the endocrine pancreas"; 1998, *FEB Letters*, vol. 229, No. 2, pp. 233-237.
Arvanitidis, Dimitriou et al.; "Can somatostatin prevent post-ERCP pancreatitis? Results of a randomized controlled trial"; 2004, *Journal of Gastroenterology and Hepatology*, vol. 19, pp. 278-282.
Bartfai, Tamas et al.; "Galanin and galanin antogonists: molecular and biochemical perspectives"; 1992, *Trends in Pharmacological Sciences*, vol. 13, No. 8, pp. 312-317.
Brook-Smith, Mark E. et al.; "Galanin is involved in the regulation of pancreatic vascular perfusion (PVP) in the anaesthetized Australian brush-tailed possum"; 2004, *J. Jap. Pancreas Soc.*, vol. 19, No. 3, p. 278, abstract.
Grendell, James H. et al.; "Receptor strategies in pancreatitis"; 1992, *The Yale Journal of Biology and Medicine*, vol. 65, pp. 431-436.
Hoogerwerf, Willemijntje A.; Pharmacological management of pancreatitis; 2005, *Current Opinion in Pharmacology*, vol. 5, pp. 578-582.
Kask, Kalev et al.; "Binding and agonist/antagonist actions of M35, galanin(1-13)-bradykinin(2-9)amide chimeric peptide, in Rin m 5F insulinoma cells"; 1995, *Regulatory Peptides*, vol. 59, pp. 341-348.
Kitagawa, Motoji et al.; "Pharmaceutical Development for Treating Pancreatic Diseases"; 1998, *Pancreas*, vol. 16, No. 3, pp. 427-431.
Langel, Ulo et al.; "Chemistry and molecular biology of galanin receptor ligands"; 1998, *Annals of the New York Academy of Sciences*, pp. 86-93.
Lindskog, Stefan et al.; "The novel high-affinity antagonist, galantide, blocks the galanin-mediated inhibition of glucose-induced insulin secretion"; 1992, *European Journal of Pharmacology*, vol. 210, pp. 183-188.
Toouli, J. et al.; "Guidelines for the management of acute pancreatitis"; 2002, *Journal of Gastroenterology and Hepatology*, vol. 17 (suppl.), pp. S15-S39.
Wang, Suke et al.; "Galanin receptor subtypes as potential therapeutic targets"; 1998, *Expert Opinion on Therapeutic Patents, Informa Healthcare*, vol. 8, No. 10, pp. 1225-1235.
Xu, Jun Xu et al.; "New high affinity peptide antagonists to the spinal galanin receptor"; 1995, *British Journal of Pharmacology*, vol. 116, pp. 2076-2080.
Yanaihara, Noboru et al.; "Galanin analogues: agonist and antagonist"; 1993, *Regulatory Peptides*, vol. 46, pp. 93-101.

* cited by examiner

*Primary Examiner* — Karen Cochrane Carlson
(74) *Attorney, Agent, or Firm* — Kilpatrick Townsend & Stockton LLP

(57) ABSTRACT

The present invention relates to a method of preventing and/or treating pancreatitis in a subject, the method including administering to the subject a therapeutically effective amount of a Galanin antagonist and/or a Galanin receptor antagonist.

15 Claims, 29 Drawing Sheets

METHODS AND COMPOSITIONS FOR PREVENTING AND/OR TREATING PANCREATITIS

CROSS-REFERENCES TO RELATED APPLICATIONS

This application is a U.S. National Stage Application of PCT/AU2006/001813, filed Dec. 1, 2006, which claims priority from Australian Provisional Patent Application No. 2005906722 filed on 1 Dec. 2005, each of which are incorporated herein by reference.

FIELD OF THE INVENTION

The present invention relates to methods and compositions for preventing and/or treating pancreatitis. The present invention also relates to a method of identifying agents that ameliorate pancreatitis.

BACKGROUND OF THE INVENTION

The pancreas is a vital gastrointestinal organ with both endocrine and exocrine functions. Acute pancreatitis is an inflammation of the pancreas that occurs when digestive enzymes leak out of the pancreatic ducts and damages the pancreas. Acute pancreatitis is a disease with significant morbidity and mortality affecting all groups. The incidence of acute pancreatitis is about 30 per 100,000, and the condition has a significant economic impact due to the need for hospitalization, including intensive care treatment.

Acute pancreatitis is a complex multi-step process consisting of early stages (trigger(s) followed by hypoperfusion, activation of proteases, lipases and amylase, and local production of inflammatory mediators) and late stages (recruitment of inflammatory cells, further tissue damage and ultimate repair or fibrosis/necrosis). Necrosis in the gland is strongly associated with a high morbidity and excruciating pain; if necrosis can be prevented or reduced, the mortality and morbidity associated with acute pancreatitis may be reduced.

Many patients also develop chronic pancreatitis with ongoing low-grade inflammation of the pancreas, progressive destruction of glandular tissue, anatomical deformities, loss of organ function and digestive capabilities, and chronic pain.

There are many putative causes of acute pancreatitis, but its typical course is reduced vascular perfusion, pancreatic ductal hypertension (often involving the bile duct) and/or hypersecretion of enzymes into the pancreatic tissue, leading to tissue autolysis. Approximately one-third of acute pancreatitis cases are associated with alcohol abuse, one-third with gallstones and one-third with other causes or lack concomitant medical conditions and are considered idiopathic. Episodes of acute pancreatitis tend to recur with resulting hospitalizations and morbidity.

Treatments for pancreatitis generally involve aggressive intravenous fluid administration to improve clinical outcomes by maintaining vascular perfusion to the gland. In addition, analgesia and antibiotics are also used in the treatment of the condition. Many studies have also concluded that ischaemia plays a major role in the development of necrosis, and so reducing ischemia may improve outcomes.

As will be appreciated, the existing treatments for acute pancreatitis are directed to maintaining vascular perfusion to the gland and the control of pain. However, pharmaceutical interventions for the treatment of acute pancreatitis remain limited. The present invention relates to methods and compositions for the prevention and/or treatment of pancreatitis.

A reference herein to a patent document or other matter which is given as prior art is not to be taken as an admission that that document or matter was, in Australia or any other country, known or that the information it contains was part of the common general knowledge as at the priority date of any of the claims.

SUMMARY OF THE INVENTION

The present invention arises out of studies into animal models of acute pancreatitis. In particular, it has been found that administration of an antagonist of Galanin or an antagonist of the Galanin receptor is able to ameliorate acute pancreatitis in these animal models.

Accordingly, the present invention provides a method of preventing and/or treating pancreatitis in a subject, the method including administering to the subject a therapeutically effective amount of a Galanin antagonist and/or a Galanin receptor antagonist.

The present invention also provides use of a Galanin antagonist and/or a Galanin receptor antagonist in the preparation of a medicament for the prevention and/or treatment of pancreatitis in a subject.

The present invention also provides a composition when used to prevent and/or treat pancreatitis in a subject, the composition including an effective amount of a Galanin antagonist and/or a Galanin receptor antagonist.

The present invention also provides a method of improving pancreatic vascular perfusion and/or reducing pancreatic inflammation in a subject, the method including administering to the subject a therapeutically effective amount of a Galanin antagonist and/or a Galanin receptor antagonist.

The present invention also provides use of a Galanin antagonist and/or a Galanin receptor antagonist in the preparation of a medicament for improving pancreatic vascular perfusion and/or reducing pancreatic inflammation in a subject.

The present invention also provides a composition when used to improve pancreatic vascular perfusion and/or reduce pancreatic inflammation in a subject, the composition including an effective amount of a Galanin antagonist and/or a Galanin receptor antagonist.

The present invention also provides a method of reducing pancreatic damage due to abnormal pancreatic vascular perfusion and/or inflammation of the pancreas in a subject, the method including administering to the subject a therapeutically effective amount of a Galanin antagonist and/or a Galanin receptor antagonist.

The present invention also provides use of a Galanin antagonist and/or a Galanin receptor antagonist in the preparation of a medicament for reducing pancreatic damage due to abnormal pancreatic vascular perfusion and/or inflammation of the pancreas in a subject.

The present invention also provides a composition when used to reduce pancreatic damage due to abnormal pancreatic vascular perfusion and/or inflammation of the pancreas in a subject, the composition including an effective amount of a Galanin antagonist and/or a Galanin receptor antagonist.

The present invention also provides a method of inhibiting progression of acute pancreatitis in a subject, the method including administering to the subject a therapeutically effective amount of a Galanin antagonist and/or a Galanin receptor antagonist.

The present invention also provides use of a Galanin antagonist and/or a Galanin receptor antagonist in the preparation of a medicament for inhibiting progression of acute pancreatitis in a subject.

The present invention also provides a composition when used to inhibit progression of acute pancreatitis in a subject, the composition including an effective amount of a Galanin antagonist and/or a Galanin receptor antagonist.

The present invention also provides a combination product including the following components:
- a Galanin antagonist and/or a Galanin receptor antagonist; and
- one or more further agents selected from the group consisting of an analgesic, including a non-narcotic and an opiate narcotic; an antibiotic; an agent that suppresses production of pancreatic enzymes, including somatostatin, octreotide, aprotinin, and gabexate mesilate; an agent that suppresses stomach acid, inclusing H2-receptor blockers and proton pump inhibitors; a pancreatic enzyme supplement; a steroid; a dehydrating fluid; an endothelin anatagonist; insulin; an agent that interferes with ICAM; a B2-Bradykinin inhibitor; a Kallikrein inhibitor; a protease activated receptor antagonist; Met RANTES; an angiotension II receptor antagonist, including candesartan; a MCP-1 synthesis blocker, including bindarit; a nitric oxide donor; a nitric oxide synthase inhibitor, including an inducible nitric oxide synthase inhibitor; an anti-ulcer agent; an ionotope; factor VII; activated protein C; calcium; glucose; a blood product including plasma and/or platelets; and butamene;

wherein the components are provided in a form for separate administration to a subject, or in a form for co-administration of one or more of the components to the subject.

The present invention also provides a pharmaceutical composition including: (i) somatostatin, or a functional variant, analogue, derivative or fragment thereof; and (ii) a Galanin antagonist and/or a Galanin receptor antagonist.

The present invention also provides a method of identifying an agent that ameliorates pancreatitis in a subject, the method including identifying an agent that is a Galanin antagonist and/or a Galanin receptor antagonist.

Various terms that will be used throughout the specification have meanings that will be well understood by a skilled addressee. However, for ease of reference, some of these terms will now be defined.

The term "Galanin" as used throughout the specification is to be understood to mean Galanin, a variant, analogue, derivative or a fragment thereof, or a fusion protein including Galanin, a, variant, analogue, derivative or a fragment thereof. The Galanin may be from any species, and may be the mature, processed form of Galanin or an immature form of Galanin (e.g., preproprotein and preprotein Galanin).

The term "Galanin antagonist" as used throughout the specification is to be understood to mean an agent that blocks, inhibits, reduces or neutralizes the function, activity and/or expression of galanin. The antagonist may function to antagonize the mature form of Galanin or an immature form.

Examples of agents in the various embodiments of the present invention include polypeptides, proteins, peptides, peptidomimetics, drugs, small molecules, large molecules, organic molecules, nucleic acids, oligonucleotides, enzymes, polysaccharides, glycoproteins, lipids, antibodies or a part thereof, and aptamers.

The term "Galanin receptor" as used throughout the specification is to be understood to mean a cell receptor that binds Galanin, including for example GALR1, GALR2 and/or GALR3, or a variant, analogue, derivative, or fragment thereof, or a fusion protein including a Galanin receptor, or a variant, analogue, derivative, or a fragment thereof.

The term "Galanin receptor antagonist" as used throughout the specification is to be understood to mean an agent that blocks, inhibits, reduces or neutralizes the function, activity and/or expression of a Galanin receptor.

The term "variant" as used throughout the specification is to be understood to mean an amino acid sequence of a polypeptide or protein that is altered by one or more amino acids. The variant may have "conservative" changes, wherein a substituted amino acid has similar structural or chemical properties to the replaced amino acid (e.g., replacement of leucine with isoleucine). A variant may also have "non-conservative" changes (e.g., replacement of a glycine with a tryptophan) or a deletion and/or insertion of one or more amino acids.

The term "subject" as used throughout the specification is to be understood to mean any multicellular organism susceptible to the development of pancreatitis, including an animal or human subject. For example, the subject may be a human or other mammal, a primate, a livestock animal (e.g. a horse, a cow, a sheep, a pig, or a goat), a companion animal (e.g. a dog, a cat), a laboratory test animal (e.g. a possum, a mouse, a rat, a guinea pig, a rabbit, a bird), an animal of veterinary significance, or an animal of economic significance.

GENERAL DESCRIPTION OF THE INVENTION

Figure 1:
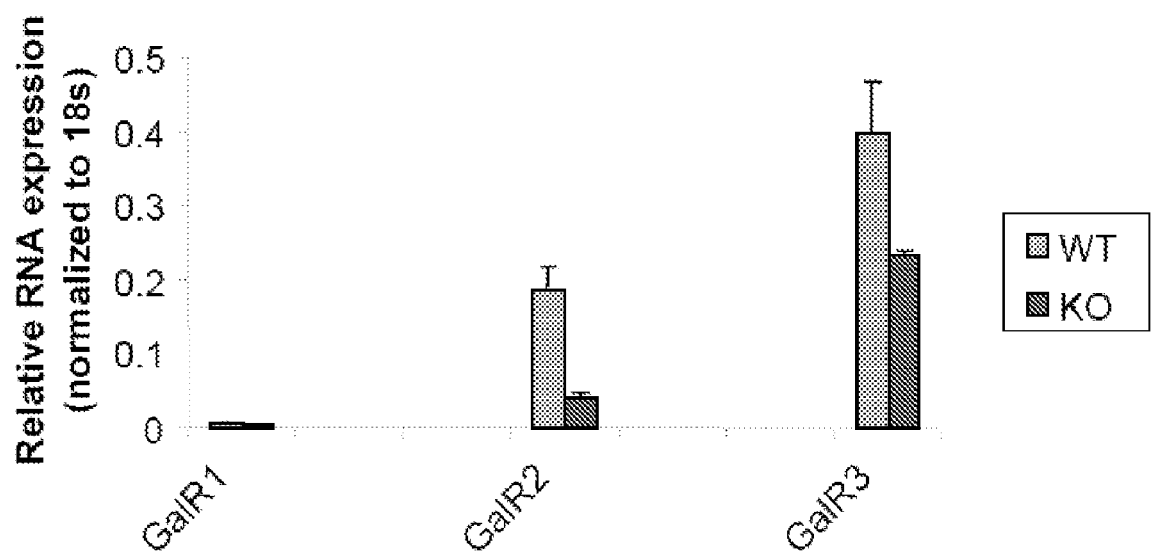
FIG. 1 shows expression of three galanin receptor (GalR) mRNA in the pancreas of wild-type and galanin knockout mice. GalR 1, 2 and 3 mRNA is expressed in the mouse pancreas. GalR3 is the most highly expressed and GalR 1 the most poorly expressed. The expression profile is similar in the galanin knockout mouse except that the expression of all three receptors appears to be reduced by about 50% (n=3 female mice). Expression is normalized to that of 18 S.

As described above, in one embodiment the present invention provides a method of preventing and/or treating pancreatitis in a subject, the method including administering to the subject a therapeutically effective amount of a Galanin antagonist and/or a Galanin receptor antagonist.

This embodiment of the present invention is directed to a method of preventing and/or treating pancreatitis in a subject by administering a Galanin antagonist and/or a Galanin receptor antagonist.

In one embodiment, the prevention and/or treatment of the pancreatitis is due to an improvement in vascular perfusion and/or a reduction in pancreatic inflammation.

Accordingly, in another embodiment the present invention provides a method of improving pancreatic vascular perfusion and/or reducing pancreatic inflammation in a subject, the method including administering to the subject a therapeutically effective amount of a Galanin antagonist and/or a Galanin receptor antagonist.

Methods for determining the extent of pancreatic vascular perfusion and determining the extent of pancreatic inflammation are known in the art.

The present invention is also suitable for reducing pancreatic damage due to abnormal pancreatic perfusion and/or inflammation of the pancreas of a subject. Methods for assessing the extent of pancreatic damage in a subject are known in the art.

Accordingly, in another embodiment the present invention provides a method of reducing pancreatic damage due to abnormal pancreatic vascular perfusion and inflammation of the pancreas of a subject, the method including administering to the subject a therapeutically effective amount of a Galanin antagonist and/or a Galanin receptor antagonist.

The present invention may be used to prevent pancreatitis in an individual at risk for developing pancreatitis. The present invention may also be used to treat pancreatitis in a subject.

The pancreatitis in the various embodiments of the present invention may be acute pancreatitis or chronic pancreatitis.

In one embodiment, the pancreatitis is acute pancreatitis. In this regard, it will be appreciated that the present invention can not only be used to treat acute pancreatitis at the time of onset, but is also suitable for prophylactic treatment of acute pancreatitis.

Acute pancreatitis may be due to a pancreatitis-inducing event such as a medical procedure, damage to the pancreas from surgery or endoscopy, damage to the pancreas from blunt or penetrating injuries, therapy including the use of drugs such as furosemide and azathioprine, sulfasalazine, and valproic acid, a pre-existing condition including hereditary pancreatitis, a gallstone, alcohol abuse, high levels of lipids (especially triglycerides) in the blood, estrogen use associated with high lipid levels, hyperparathyroidism and high levels of calcium in the blood, reduced blood supply to the pancreas, for example, from severely low blood pressure, a disease or condition including Mumps, pancreatic cancer, and kidney transplantation.

Chronic pancreatitis may be due to alcohol abuse or alcoholism, blocked or narrowed pancreatic duct because of trauma or pseudocysts, heredity reasons, or be due to an unknown cause (idiopathic). Other causes of chronic pancreatitis are congenital conditions such as pancreas divisum, cystic fibrosis, high levels of calcium in the blood (hypercalcemia), high levels of blood fats (hyperlipidemia or hypertriglyceridemia), the use of some drugs and certain autoimmune conditions.

Diagnosis and evaluation of pancreatitis in a subject may be performed by a suitable method known in the art by an appropriate practitioner. Clinical indications of pancreatitis include for example abdominal pain which may radiate to the back, hyperhydrolesemia, elevated serum levels of amylase, isoamylase, lipase, C-reactive protein, trypsinogen-2, trypsin, phospholipase $A_2$, and/or trypsin-2-alpha 1 antitrypsin complex. Scoring systems, such as the Ranson, Osborne and Apache II scoring systems, may also be used to diagnose pancreatitis in a patient, alone or in conjunction with visualization technologies, such as ultrasonography, CT scan, and ERCP.

The present invention may also be used to inhibit the exacerbation of a pre-existing pancreatic condition.

Accordingly, in another embodiment the present invention provides a method of inhibiting progression of pancreatitis in a subject, the method including administering to the subject a therapeutically effective amount of a Galanin antagonist and/or a Galanin receptor antagonist.

In this embodiment, the present invention may be used for example to inhibit the progression of mild pancreatitis to acute pancreatitis, and/or the progression of acute pancreatitis to severe acute pancreatitis (necrotizing pancreatitis).

The subject in the various forms of the present invention is any multicellular organism susceptible to the development of, or actually suffering from, pancreatitis, including an animal or human subject. For example, the subject may be a human or other mammal, a primate, a livestock animal (e.g. a horse, a cow, a sheep, a pig, or a goat), a companion animal (e.g. a dog, a cat), a laboratory test animal (e.g. a possum, a mouse, a rat, a guinea pig, a rabbit, a bird), an animal of veterinary significance, or an animal of economic significance.

In one embodiment, the method of the present invention is for the prevention and/or treatment of pancreatitis in a mammalian subject. For example, the present invention may be used for the prevention and/or treatment of pancreatitis in a human subject.

As described above, the subject in the various embodiments of the present invention may be a subject suffering from pancreatitis, or be a subject at risk of developing pancreatitis. In one embodiment, the subject is a human suffering from, or at risk of developing, acute pancreatitis.

The present invention involves the administration to a subject of a Galanin antagonist and/or a Galanin receptor antagonist.

Galanin is a 29 amino acid C-terminally amidated peptide (30 amino acid, non-amidated in humans), highly conserved but unique neuroendocrine peptide originally isolated from intestine. The first 14 amino acids are fully conserved in almost all species. Galanin is generally found in the brain and the gut. Galanin mRNA is translated to a larger polypeptide, prepro-galanin, which contains a signal peptide, galanin, and 59-60 amino acid long C-terminally amidated flanking peptide called GMAP (Galanin mRNA associated peptide). Several N-terminally elongated (−7-29 and −9-29) or truncated biologically active forms of galanin have also been isolated.

```
                                        (SEQ ID NO: 11)
Human Galanin has the sequence H-Gly-Trp-Thr-Leu- Asn-Ser-Ala-Gly-Tyr-Leu-Leu-Gly-Pro-His-Ala-Val- Gly-Asn-His-Arg-Ser-Phe-Ser-Asp-Lys-Asn-Gly-Leu- Thr-Ser-OH.
```

The nucleotide and/or amino acid sequences of galanin peptides can be found in the literature or public databases, or the nucleotide and/or amino acid sequences can be determined using cloning and sequencing techniques known to one of skill in the art. For example, the nucleotide sequence of human galanin can be found at GenBank Accession Nos. A28025 and NM_015973. The amino acid sequence of human galanin can be found at GenBank Accession Nos. CAA01907, NP_057057, P22466 and AAH30241.

Other accession numbers for galanin from other species are as follows:
*Bos taurus* NP_776339 (consists of amino acid residues 33-61)
*Homo sapiens* (preproprotein) AAH30241
*Homo sapiens* AAB20740
*Rattus norvegicus* NP_150240 (consists of amino acid residues 33-62)
*Mus musculus* NP_034383

Methods for identifying other Galanin peptides are known in the art. For example, the peptides or the genes encoding the peptide may be identified using the BLAST algorithm, which determines the extent of homology between two nucleotide sequences (blastn) or the extent of homology between two amino acid sequences (blastp). BLAST identifies local alignments between the sequences in the database and predicts the probability of the local alignment occurring by chance. The BLAST algorithm is as described in Altschul et al. (1990) *J. Mol. Biol.* 215:403-410.

The Galanin antagonist in the various embodiments of the present invention may be an antagonist to Galanin from a suitable species. In one embodiment, the antagonist is an antagonist of human Galanin.

As described previously herein, the Galanin antagonist in the various forms of the present is an agent that blocks, inhibits, reduces or neutralizes the function, activity and/or expression of galanin. The antagonist may function to antagonize the mature form of Galanin or an immature form. Methods for identifying Galanin antagonists are known in the art.

Examples of Galanin antagonists include polypeptides, proteins, peptides, peptidomimetics, non-peptide molecules, drugs, small molecules, large molecules, organic molecules, nucleic acids, oligonucleotides, enzymes, polysaccharides, glycoproteins, lipids, antibodies or a part thereof, and aptamers.

In one embodiment the Galanin antagonist is a peptide antagonist. Examples of galanin antagonists in the various embodiments of the present invention include Galantide (M15; Galanin(1-13)-substance P(5-11) amide; Ogren et al. (1993) *Eur J. Pharmacol* 242(1):59-64); C7 (Galanin(1-13)-spantide amide; Xu et al. (1995) *Br J. Pharmacol* 116(3): 2076-2080); M40 (Galanin(1-13)-Pro-Pro-Ala-Leu-Ala-Leu-Ala amide; Xu et al. (1995) *Br J. Pharmacol* 116(3): 2076-2080); M35 (Kask et al. (1995) *Regul Pept.* 59(3):341-348); M38 (Galanin(1-13)-(Ala-Leu)$_3$-Ala amide; Xu et al. (1995) *Br J. Pharmacol* 116(3):2076-2080); and M32 (Galanin(1-13)-Pro-Pro-Ala-Leu-Ala-Leu-Ala amide). These galanin antagonists are chimeric peptides generated by linking the amino terminal portion of galanin to substance P (galantide, M15), bradykinin (M35), the neurokinin antagonist spantide (C7) or an idealized alpha helical region (M40).

Sequences of the M15, C7, M40, M35 and M32 antagonists are as follows:

```
M15:
GWTLNSAGYLLGPQQFFGLM              (SEQ ID NO: 12)

C7:
GWTLNSAGYLLGPrPKPQQwFwLL          (SEQ ID NO: 13)
(lower case amino acids are D-amino acids)

M40:
GWTLNSAGYLLGPPPALALA              (SEQ ID NO: 14)

M35:
GWTLNSAGYLLGPPPGFSPFR             (SEQ ID NO: 15)

M32:
GWTLNSAGYLLGPRHYINLITRQRY         (SEQ ID NO: 16)
```

In one embodiment, the Galanin antagonist in the various forms of the present invention is Galantide (M15), or a variant, analogue, derivative, or fragment thereof, all of which are functional.

In another embodiment, the Galanin antagonist is M871 (Sollenberg et al. (2006) *International Journal of Peptide Research and Therapeutics* 12(2):115-119).

In one embodiment, the Galanin antagonist has at least 80% sequence identity to one of M15; C7; M40; M38; M35; M32 and M871. In one specific embodiment, the Galanin antagonist has at least 90% sequence identity to one of M15; C7; M40; M38; M35; M32 and M871. Methods for determining the extent of sequence identity are known in the art, and include the BLAST algorithm as previously hereinbefore described.

In one embodiment, the Galanin antagonist has at least 80% sequence identity to Galantide, for example at least 90% sequence identity to Galantide.

In another embodiment, the Galanin antagonist is a non-peptide antagonist, such as SNAP 37889 or SNAP 398299 (Swanson et al. (2005) *Proc. Natl. Acad. Sci. USA* 102: 17489-17494).

Galanin mediates its biological effects by interacting with high affinity cell surface receptors. Pharmacological studies suggest the existence of multiple receptor subtypes, and three galanin receptors (GALR1, GALR2, and GALR3) have been cloned thus far. These receptors belong to the family of G-protein coupled receptor superfamily, characterized by seven transmembrane domains.

GALR1 in human is 349 amino acids in length and is located at chromosome 15q24. It has 55-70 kDa non-glycosylated and glycosylated forms and shares 92% sequence conservation with rat. GALR1 has high affinity for galanin (Kd=0.07 nM), N-terminal galanin fragments, and putative galanin receptor antagonists galantide, C7, M35, and M40. C-terminal galanin fragments do not bind to GALR1.

GALR2 in human is 387 amino acids in length and is located at chromosome 17q25.3. The rat and human GALR2 are ~87% conserved. GALR2 binds galanin, N-terminal galanin fragments, and chimeric peptides. Galanin 2-29 binds GALR2 with higher affinity than GALR1.

Human GALR3 encodes a protein of 368 amino acids. The rat and human GALR3 are ~90% conserved. The affinity of various peptides for GALR3 is as described in Smith et al (1998) *J. Biol. Chem.* 273(36):23321-23326.

Methods for identifying Galanin receptors are known in the art. For example, the protein or the genes encoding the protein may be identified using the BLAST algorithm, as previously hereinbefore described.

The nucleotide sequence of human GALR1, human GALR2 and human GALR3 can be found in at GenBank Accession Nos. NM_001480, AF080586 and NM_003857, respectively. The amino acid sequence of human GALR1, human GALR2 and human GALR3 can be found at GenBank Accession Nos. NP_001471, NP_003848, and NP_060755.

Accession number for other Galanin receptors are as follows:
*Homo sapiens* Galanin receptor 1 NM_001480
*Homo sapiens* Galanin receptor 2 O43603
*Homo Sapiens* Galanin receptor 2 JC5949
*Homo Sapiens* Galanin receptor 3 O60755
*Homo Sapiens* Galanin receptor 3 NP_003605
*Rattus norvegicus* Galanin receptor 1 NP_037090
*Rattus norvegicus* Galanin receptor 2 NP_062045
*Rattus norvegicus* Galanin receptor 3 XP_346808
*Rattus norvegicus* Galanin receptor 3 NP_062046
*Mus inusculus* Galanin receptor 1 P56479
*Mus inusculus* Galanin receptor 1 NP_032108
*Mus inusculus* Galanin receptor 2 AAC36589
*Mus inusculus* Galanin receptor 3. NP_056553

The Galanin receptor antagonist in the various embodiments of the present invention may be an antagonist to a Galanin receptor from a suitable species.

In one embodiment, the Galanin receptor antagonist is an antagonist of a human Galanin receptor.

As described previously herein, the Galanin receptor antagonist as used throughout the specification is to be understood to mean an agent that blocks, inhibits, reduces or neutralizes the function, activity and/or expression of a Galanin receptor. Methods for identifying Galanin receptor antagonists are known in the art.

Examples of Galanin receptor antagonists include polypeptides, proteins, peptides, peptidomimetics, non-peptide molecules, drugs, small molecules, large molecules, organic molecules, nucleic acids, oligonucleotides, enzymes, polysaccharides, glycoproteins, lipids, antibodies or a part thereof, and aptamers.

In one embodiment, the Galanin receptor antagonist is a peptide antagonist.

In another embodiment, the Galanin receptor antagonist is a non-peptide antagonist.

In one embodiment, the Galanin receptor antagonist is an antagonist of one or more of GalR1, GalR2 and GalR3.

Examples of Galanin receptor antagonists in the various forms of the present invention include M15 (Galantide), M35, M40, C7, M32, M38, M871, D-Thr$^6$, [D-Trp$^{8,9}$]-Galanin(1-15)ol, [D-Trp$^{8,9}$]-Galanin(1-15)ol, SCH-202596 (Spirocoumaranon), Dithiin-1,1,4,4-tetroxide, and SNAP 37889 and SNAP 398299 (Gal3 receptor antagonists as described in Swanson et al. (2005) *Proc. Natl. Acad. Sci. USA* 102: 17489-17494).

In one embodiment, the Galanin receptor antagonist is Galantide, or a functional variant, analogue, derivative, or fragment thereof.

In one embodiment, the Galanin receptor antagonist has at least 80% sequence identity to one of M15, C7, M40, M38, M35, M32 and M871. In one specific embodiment, the Galanin receptor antagonist has at least 90% sequence identity to one of M15, C7, M40, M38, M35, M32 and M871.

In one embodiment, the Galanin receptor antagonist has at least 80% sequence identity to Galantide. In one specific embodiment, the Galanin receptor antagonist has at least 90% sequence identity to Galantide.

Examples of other antagonists include "Galnon" as described in United Sates patent application 20030055000, and 2,3-Dihydro-dithiin and -dithiepine-1, 1,4,4-tetroxides (Scott et al. (2000) *Bioorg Med Chem.* 8(6):1383-91; GalR1 antagonists).

To prepare pharmaceutical compositions including a Galanin antagonist and/or a Galanin receptor antagonist for use in the various embodiments of the present invention, the antagonist will typically be admixed with a pharmaceutically acceptable carrier or excipient, which are preferably inert. A pharmaceutical carrier can be any compatible non-toxic substance suitable for delivery of the polypeptide to a subject. Preparation of such pharmaceutical compositions is known in the art, for example Remington's Pharmaceutical Sciences, 18th ed., 1990, Mack Publishing Co., Easton, Pa. and U.S. Pharmacopeia: National Formulary, 1984, Mack Publishing Company, Easton, Pa.

Accordingly, in another embodiment the present invention provides a composition when used to prevent and/or treat pancreatitis in a subject, the composition including an effective amount of a Galanin antagonist and/or a Galanin receptor antagonist.

The Galanin antagonist and/or the Galanin receptor antagonist may also be used in the preparation of a medicament for the prevention and/or treatment of pancreatitis in a subject.

Accordingly, in another embodiment the present invention provises use of a Galanin antagonist and/or a Galanin receptor antagonist in the preparation of a medicament for preventing and/or treating pancreatitis in a subject.

As described above, the Galanin antagonist and/or the Galanin receptor antagonist may be used in the preparation of a composition or a medicament for improving vascular perfusion and/or reducing pancreatic inflammation in a subject.

Accordingly, in another embodiment the present invention provides a composition when used to improve vascular perfusion and/or reduce pancreatic inflammation in a subject, the composition including an effective amount of a Galanin antagonist and/or a Galanin receptor antagonist.

The Galanin antagonist and/or the Galanin receptor antagonist may also be used in the preparation of a medicament for improving vascular perfusion and/or reducing pancreatic inflammation in a subject.

Accordingly, in another embodiment the present invention provides use of a Galanin antagonist and/or a Galanin receptor antagonist in the preparation of a medicament for improving vascular perfusion and/or reducing pancreatic inflammation in a subject.

The Galanin antagonist and/or the Galanin receptor antagonist may also be used in the preparation of a composition or a medicament for reducing pancreatic damage due to abnormal pancreatic vascular perfusion and inflammation of the pancreas in a subject.

Accordingly, in another form the present invention provides a composition when used to reduce pancreatic damage due to abnormal pancreatic vascular perfusion and inflammation of the pancreas in a subject, the composition including an effective amount of a Galanin antagonist and/or a Galanin receptor antagonist.

The Galanin antagonist and/or the Galanin receptor antagonist may also be used in the preparation of a medicament for reducing pancreatic damage due to abnormal pancreatic vascular perfusion and inflammation of the pancreas in a subject.

Accordingly, in another embodiment the present invention provises use of a Galanin antagonist and/or a Galanin receptor antagonist in the preparation of a medicament for reducing pancreatic damage due to abnormal pancreatic vascular perfusion and inflammation of the pancreas in a subject.

The Galanin antagonist and/or the Galanin receptor antagonist may also be used in the preparation of a composition or a medicament for inhibiting progression of pancreatitis to a more severe form in a subject.

Accordingly, in another form the present invention provides a composition when used to inhibit progression of pancreatitis in a subject, the composition including an effective amount of a Galanin antagonist and/or a Galanin receptor antagonist.

The Galanin antagonist and/or the Galanin receptor antagonist may also be used in the preparation of a medicament for inhibiting progression of pancreatitis to a more severe form in a subject.

Accordingly, in another embodiment the present invention provises use of a Galanin antagonist and/or a Galanin receptor antagonist in the preparation of a medicament for inhibiting progression of pancreatitis to a more severe form in a subject.

In the case of administration of a Galanin antagonist and/or a Galanin receptor antagonist to a human or animal subject, the antagonist may be administered to the subject in a suitable form.

The effective amount of antagonist to be administered is not particularly limited, so long as it is within such an amount and in such a form that generally exhibits a useful or therapeutic effect. The term "therapeutically effective amount" is the quantity which, when administered to a subject in need of treatment, improves the prognosis of the subject, e.g., delays the onset of and/or reduces the severity of one or more of the subject's symptoms associated with a pancreatitis. The amount to be administered to a subject will depend on the particular characteristics of the disease, the mode of administration, and the characteristics of the subject, such as general health, other diseases, age, sex, genotype, body weight and tolerance to drugs. A person skilled in the art will be able to determine appropriate dosages depending on these and other factors. Effective amounts of the antagonists typically range between about 0.1 mg/kg body weight per day and about 1000 mg/kg body weight per day, and usually between 1 mg/kg body weight per day and 100 mg/kg body weight per day.

In one embodiment, the dose of the antagonist administered to the subject is in the range from 0.1 nmol/kg to 100 nmol/kg. In one specific embodiment, the dose of the antagonist administered to the subject is in the range from 1 nmol/kg to 50 nmol/kg, such as a dose of the antagonist in the range from 5 nmol/kg to 50 nmol/kg.

The antagonist may be administered alone or in combination ("co-administered") with one or more of the other agents, such as gabexate mesylate and somatostatin. The co-administration can be sequential or simultaneous. "Co-administration" generally means that the multiple (two or more) therapeutics are present in the subject during a specified time interval. Typically, if a second agent is administered within the half-life of the first agent, the two agents are considered co-administered.

In one embodiment, the co-administration is in the form of a single composition for administration to the subject.

Accordingly, in another embodiment the present invention provides a composition including a galanin antagonist and/or a galanin receptor antagonist and one or more of the agents selected from the group consisting of an analgesic (including non-narcotic medications such as acetaminophen and/or ibuprofen and opiate narcotics such meperidine (Demerol) or morphine); an antibiotic; an agent that suppresses production of pancreatic enzymes (including somatostatin, octreotide, aprotinin, and gabexate mesilate); an agent that suppresses stomach acid (including H2-receptor blockers (eg Tagamet, Pepcid, or Zantac) and proton pump inhibitors (eg Prilosec or Prevacid); pancreatic enzyme supplements; a steroid; a dehydrating fluid; an endothelin anatagonist; insulin; an agent that interferes with ICAM (including antibodies); B2-Bradykinin and Kallikrein inhibitors; a protease activated receptor antagonist; Met RANTES; angiotension II receptor antagonists (e.g. candesartan); a MCP-1 synthesis blocker (e.g. bindarit); a nitric oxide donor; a nitric oxide synthase inhibitor, including inducible nitric oxide synthase inhibitors; an anti-ulcer agent; an ionotope; factor VII; activated protein C; calcium; glucose; a blood product including plasma and/or platelets; and butamene.

In another embodiment, the co-administration is by way of a combination product for separate administration to a subject, or for co-administration to the subject Accordingly, in another form the present invention also provides a combination product including the following components:

a galanin antagonist and/or a galanin receptor antagonist; and one or more further agents selected from the group consisting of an analgesic (including non-narcotic medications such as acetaminophen and/or ibuprofen and opiate narcotics such meperidine (Demerol) or morphine); an antibiotic; an agent that suppresses production of pancreatic enzymes (including somatostatin, octreotide, aprotinin, and gabexate mesilate); an agent that suppresses stomach acid (including H2-receptor blockers (eg Tagamet, Pepcid, or Zantac) and proton pump inhibitors (eg Prilosec or Prevacid); pancreatic enzyme supplements; a steroid; a dehydrating fluid; an endothelin anatagonist; insulin; an agent that interferes with ICAM (including antibodies); B2-Bradykinin and Kallikrein inhibitors; a protease activated receptor antagonist; Met RANTES; angiotension II receptor antagonists (e.g. candesartan); a MCP-1 synthesis blocker (e.g. bindarit); a nitric oxide donor; a nitric oxide synthase inhibitor, including inducible nitric oxide synthase inhibitors; an anti-ulcer agent; an ionotope; factor VII; activated protein C; calcium; glucose; a blood product including plasma and/or platelets; and butamene;

wherein the components are provided in a form for separate administration to a subject, or in a form for co-administration of one or more of the components to the subject.

The combination product is suitable preventing and/or treating pancreatitis in a subject, for improving pancreatic vascular perfusion and/or reducing pancreatic inflammation in a subject, for reducing pancreatic damage due to abnormal pancreatic vascular perfusion and/or inflammation of the pancreas in a subject, and for inhibiting progression of acute pancreatitis in a subject.

The administration of the antagonist, or a composition including the antagonist, may be within any time suitable to produce the desired effect, for example preventing and/or treating pancreatitis.

Suitable dose regimens of the antagonist to treat pancreatitis may be, for example, in the range of about 0.1 nmol/kg to 100 nmol/kg per day intravenously, subcutaneously or intramuscularly in divided doses from 3 to 6 times per day. A continuous infusion of the antagonist achieving a cumulative daily dose in this range may also be used. Oral, sublingual and transdermal doses would be higher based on relative bioavailability to intravenous administration.

The administration of the antagonist to the subject in the various embodiments of the present invention is at one or more of prior to the onset of the pancreatitis, concurrently with the onset of pancreatitis, and in the early phase of the pancreatitis.

In one embodiment, the antagonist is administered with 24 hours of the onset of the pancreatitis, typically within 12 hours of the onset of pancreatitis, such as within 3 hours of the onset of the pancreatitis.

For example, in the case of acute pancreatitis, the antagonist may be administered as soon after diagnosis of acute pancreatitis as possible and given daily (for example in divided doses or continuous infusion) for about 3 days to about 14 days.

The antagonist may be administered by a suitable route, including administration orally, parenterally, topically or by any other suitable means, and therefore transit time of the antagonist must also be taken into account.

As described above, the administration of the antagonist may also include the use of one or more pharmaceutically acceptable additives, including pharmaceutically acceptable salts, amino acids, polypeptides, polymers, solvents, buffers, excipients and bulking agents, taking into consideration the particular physical and chemical characteristics of the antagonist to be administered.

For example, the antagonist can be prepared into a variety of pharmaceutical compositions in the form of, e.g., an aqueous solution, an oily preparation, a fatty emulsion, an emulsion, a gel, etc., and these preparations can be administered as intramuscular or subcutaneous injection or as injection to an organ, or as an embedded preparation or as a transmucosal preparation through nasal cavity, rectum, uterus, vagina, lung, etc. The composition may be administered in the form of oral preparations (for example solid preparations such as tablets, capsules, granules or powders; liquid preparations such as syrup, emulsions or suspensions). Compositions containing the antagonist may also contain a preservative, stabiliser, dispersing agent, pH controller or isotonic agent. Examples of suitable preservatives are glycerin, propylene glycol, phenol or benzyl alcohol. Examples of suitable stabilisers are dextran, gelatin, a-tocopherol acetate or alpha-thioglycerin. Examples of suitable dispersing agents include polyoxyethylene (20), sorbitan mono-oleate (Tween 80), sorbitan sesquioleate (Span 30), polyoxyethylene (160) polyoxypropylene (30) glycol (Pluronic F68) or polyoxyethylene hydrogenated castor oil 60. Examples of suitable pH controllers include hydrochloric acid, sodium hydroxide and the like. Examples of suitable isotonic agents are glucose, D-sorbitol or D-mannitol.

The administration of the antagonist in the various embodiments of the present invention may also be in the form of a composition containing a pharmaceutically acceptable carrier, diluent, excipient, suspending agent, lubricating agent, adjuvant, vehicle, delivery system, emulsifier, disintegrant, absorbent, preservative, surfactant, colorant, flavorant or sweetener, taking into account the physical and chemical properties of the antagonist being administered.

For these purposes, the composition may be administered orally, parenterally, by inhalation spray, absorption, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally acceptable diluents or solvents, for example, as solutions in 1,3-butanediol. Among the acceptable vehicles and solvents that may be employed are water, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

The carrier may contain minor amounts of additives, such as substances that enhance solubility, isotonicity, and chemical stability, for example anti-oxidants, buffers and preservatives.

When administered orally, the antagonist will usually be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semi-solid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

A tablet may be made by compressing or molding the antagonist optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Moulded tablets may be made by moulding in a suitable machine, a mixture of the powdered active ingredient and a suitable carrier moistened with an inert liquid diluent.

The administration of the antagonist may also utilize controlled release technology. The antagonist may also be administered as a sustained-release pharmaceutical. To further increase the sustained release effect, the antagonist may be formulated with additional components such as vegetable oil (for example soybean oil, sesame oil, camellia oil, castor oil, peanut oil, rape seed oil); middle fatty acid triglycerides; fatty acid esters such as ethyl oleate; polysiloxane derivatives; alternatively, water-soluble high molecular weight compounds such as hyaluronic acid or salts thereof (weight average molecular weight: ca. 80,000 to 2,000,000), carboxymethylcellulose sodium (weight average molecular weight: ca. 20,000 to 400,000), hydroxypropylcellulose (viscosity in 2% aqueous solution: 3 to 4,000 cps), atherocollagen (weight average molecular weight: ca. 300,000), polyethylene glycol (weight average molecular weight: ca. 400 to 20,000), polyethylene oxide (weight average molecular weight: ca. 100,000 to 9,000,000), hydroxypropylmethylcellulose (viscosity in 1% aqueous solution: 4 to 100,000 cSt), methylcellulose (viscosity in 2% aqueous solution: 15 to 8,000 cSt), polyvinyl alcohol (viscosity: 2 to 100 cSt), polyvinylpyrrolidone (weight average molecular weight: 25,000 to 1,200,000).

Alternatively, the antagonist may be incorporated into a hydrophobic polymer matrix for controlled release over a period of days. The antagonist may then be moulded into a solid implant, or externally applied patch, suitable for providing efficacious concentrations of the antagonist over a prolonged period of time without the need for frequent re-dosing. Such controlled release films are well known to the art. Other examples of polymers commonly employed for this purpose that may be used include nondegradable ethylene-vinyl acetate copolymer a degradable lactic acid-glycolic acid copolymers, which may be used externally or internally. Certain hydrogels such as poly(hydroxyethylmethacrylate) or poly(vinylalcohol) also may be useful, but for shorter release cycles than the other polymer release systems, such as those mentioned above.

The carrier may also be a solid biodegradable polymer or mixture of biodegradable polymers with appropriate time-release characteristics and release kinetics. The antagonist may then be moulded into a solid implant suitable for providing efficacious concentrations of the antagonist over a prolonged period of time without the need for frequent re-dosing. The antagonist can be incorporated into the biodegradable polymer or polymer mixture in any suitable manner known to one of ordinary skill in the art and may form a homogeneous matrix with the biodegradable polymer, or may be encapsulated in some way within the polymer, or may be moulded into a solid implant.

For topical administration, the composition of the present invention may be in the form of a solution, spray, lotion, cream (for example a non-ionic cream), gel, paste or ointment. Alternatively, the composition may be delivered via a liposome, nanosome, rivosome, or nutri-diffuser vehicle.

It should also be appreciated that other methods for delivery of an antagonist are contemplated. For example, the antagonist may be delivered by way of a nucleic acid or vector that allows for expression of the antagonist in the appropriate target cells. For example, the antagonist may be delivered by way of a viral vector that causes expression of the antagonist in target cells. The antagonist can also be delivered by standard gene therapy techniques, including e.g., direct DNA injection into tissues, the use of recombinant viral vectors or phospholipid and implantation of transfected cells, for example as described in Rosenberg, *J. Clin. Oncol.* 10:180 (1992).

As described above, the Galanin antagonist and/or the Galanin receptor antagonist may also be used in combination with another agent selected from the group consisting of an analgesic (including non-narcotic medications such as acetaminophen and/or ibuprofen and opiate narcotics such meperidine (Demerol) or morphine); an antibiotic; an agent that suppresses production of pancreatic enzymes (including somatostatin, octreotide, aprotinin, and gabexate mesilate); an agent that suppresses stomach acid (including H2-receptor blockers (e.g. Tagamet, Pepcid, or Zantac) and proton pump inhibitors (eg Prilosec or Prevacid); pancreatic enzyme supplements; a steroid; a dehydrating fluid; an endothelin anatagonist; insulin; an agent that interferes with ICAM (including antibodies); B2-Bradykinin and Kallikrein inhibitors; a protease activated receptor antagonist; Met RANTES; angiotension II receptor antagonists (e.g. candesartan); a MCP-1 synthesis blocker (e.g. bindarit); a nitric oxide donor; a nitric oxide synthase inhibitor, including inducible nitric oxide synthase inhibitors; an anti-ulcer agent; an ionotope; factor VII; activated protein C; calcium; glucose; a blood product including plasma and/or platelets; and butamene;

In one specific embodiment, the Galanin antagonist may be used in combination with somatostatin, or a function variant, analogue, derivative or fragment thereof.

Accordingly, in another embodiment the present invention also provides a method as previously hereindescribed of preventing and/or treating pancreatitis in a subject, improving pancreatic vascular perfusion and/or reducing pancreatic inflammation in a subject, reducing pancreatic damage due to abnormal pancreatic vascular perfusion and/or inflammation of the pancreas in a subject, or inhibiting progression of acute pancreatitis in a subject, the method further including administering an effective amount of somatostatin, or a function variant, analogue, derivative or fragment thereof.

In another embodiment the present invention provides a pharmaceutical composition including: (i) somatostatin, or a functional variant, analogue, derivative or fragment thereof; and (ii) a Galanin antagonist and/or a Galanin receptor antagonist.

In this regard, somatostatin (somatotropin release inhibiting factor or SRIF) has both a 14 amino acid isoform (somatostatin-14) and a 28 amino acid isoform (somatostatin-28), as described for example in Wilson, J. & Foster, D., Williams Textbook of Endocrinology, p. 510 (7th ed., 1985).

Methods for administering somatostatin, and suitable dosages, are as previously described herein. A suitable dose of somatostation is 50 µg to 1000 µg (eg 250 µg) delivered as an intravenous bolus injection (Somatostatin-UCB; UCB Pharma, Brussels, Belgium).

Somatostatin and variants, analogues, derivatives and fragments are as described in "Somatostatin" (2004) edited by Coimbature B. Srikant, Kluwer Academic Publishers.

The present invention is also suitable for identifying agents that have the ability to ameliorate pancreatitis in a subject.

Accordingly, in another form the present invention provides a method of identifying an agent that ameliorates pancreatitis in a subject, the method including identifying an agent that is a Galanin antagonist and/or a Galanin receptor antagonist.

The identification of agents that antagonize the function or activity of Galanin and/or a Galanin receptor may be performed by a suitable method. Galanin receptor antagonists may be tested in a variety of in vivo and in vitro models of galanin action, for example as described in Liu et al. (1998) *J Biomol Screen* 3:199-206, or as described in US patent application 20050026213.

For example, screening of galanin type 1 receptor (hGalR1) antagonists may be performed using a CHO cell line stably co-transfected with human GalR1 and a luciferase reporter gene under the control of serum response elements (SREs). Agonist (eg 10 nM human galanin) stimulation of hGalR1 causes an increase in luciferase expression, detected as increased enzyme activity, which is blocked by putative antagonists.

Such screening systems provide methods for bringing together a mammalian galanin receptor, galanin, and an agent to be tested as a galanin antagonist.

Two basic types of screening systems can be used, a labeled-ligand binding assay and a "functional" assay. A labeled ligand for use in the binding assay can be obtained by labeling galanin with a measurable group, such as $I^{125}$ by methods known in the art. Methods for the determination of the ability of a molecule to act as an antagonist in such labeled-ligand assays are also known in the art.

In a basic binding assay, the method for identifying a galanin antagonist includes contacting a GalR receptor in the presence of a known amount of labeled galanin with an agent to be tested as an antagonist, and measuring the amount of labeled galanin bound to the receptor, and identifying an antagonist by measuring substantially reduced binding of the labeled galanin to the GalR receptor, compared to what would be measured in the absence of such an antagonist.

In cellular models, parameters for intracellular activities mediated by galanin receptors can be monitored for antagonistic activities to screen for antagonists. Such parameters include intracellular second messenger pathways activated via the GalR receptors, changes in cell growth rate, secretion of hormones, etc., using methods known in the art. Examples of methods of measurement of the effects of the ligands on receptor-mediated inhibition of forskolin-stimulated intracellular cAMP production (Parker et al. (1995) *Mol. Brain Res.* 34:179-189), receptor-stimulated $Ca^{++}$ mobilization and mitogenic effects Sethi et al. (1991) *Cancer Res.* 51:1674-1679), and receptor-mediated glucose-stimulated insulin release (Yanaihara et al. (1993) *Regulatory Peptides* 46:93-101).

The present invention also provides an agent identified according to the screening method hereinbefore described, and the use of such agents for preventing and/or treating pancreatitis in a subject, for improving pancreatic vascular perfusion and/or reducing pancreatic inflammation in a subject, for reducing pancreatic damage due to abnormal pancreatic vascular perfusion and/or inflammation of the pancreas in a subject, and for inhibiting progression of acute pancreatitis in a subject.

DESCRIPTION OF SPECIFIC EMBODIMENTS

Reference will now be made to experiments that embody the above general principles of the present invention. However, it is to be understood that the following description is not to limit the generality of the above description.

Example 1

Animals

Australian Brush-tailed possums (*Trichosurus vulpecula*) of either sex weighing between 1.5 and 3 kg were used for acute pancreatitis experiments. All animals were fasted overnight with access to water prior to use. The study was approved by the Animal Welfare Committee of the Flinders University (approval number #603/05).

Example 2

Surgical Procedures

After intramuscular anaesthetics (ketamine, 20 mg/kg, Ketamil Injection, Troy Laboratories Pty. Ltd., NSW, Australia; xylazine, 5 mg/kg, Rompun, Bayer Australia Ltd., NSW, Australia) the animals were shaved with an electric razor over the neck, abdomen and the inguinal regions. The animal was then placed on a heating blanket to maintain the temperature at 37° C. (Harvard Apparatus, Holliston, Mass., USA). A tracheostomy was performed and the animal was ventilated with a small animal ventilator (Harvard Apparatus, Holliston, Mass., USA). The left femoral vein was cannulated with two cannulas (1.05 mm outside diameter (OD), 0.35 mm internal diameter (ID)) for delivery of anaesthetic and normal saline. Anaesthesia was maintained with an intravenous infusion of sodium thiopentone (Pentothal, Abbott Australia Pty Ltd, Kurnell, NSW, Australia), initially at a 2 ml/kg/h and then titrated to maintain anaesthesia for the duration of experiment. Normal saline is given at 4 ml/hr to maintain the hydration state of the animal. Left femoral artery was cannulated (1.5 mm OD, 0.9 mm ID) and connected to a pressure transducer (Transpac IV, Abbot Ireland, Sligo, Republic of Ireland) to continuously measure blood pressure. Two catheters (1.5 mm OD, 0.9 mm ID) were placed into the right femoral vein; one was advanced into the inferior vena cava in the thorax and connected to a pressure transducer in order to monitor central venous pressure and the other catheter was used for drug infusion. Right femoral artery was also cannulated (1.5 mm OD, 0.9 mm ID) to collect blood samples for enzymatic analysis. A urinary catheter was inserted into the bladder to allow urine drainage during the experiment. The abdomen was opened by midline incision. With minimal handling of tissues, the duodenum with the sphincter of Oddi was placed on a platform and stabilised. The pancreatic duct part of the sphincter of Oddi was identified with the aid of a dissecting microscope. The pancreatic duct part of sphincter of Oddi was then opened with the help of micro scissors. It was then cannulated (1.5 mm OD, 0.9 mm ID) for 4-5 mm and ligated with 5-0 prolene. The cannula was then connected to a pressure transducer to record the pancreatic duct pressure and provided a "functional ligation".

Example 3

Pancreatic Duct Pressure

When the pancreatic duct was cannulated the pressure within it gradually rose to 7-8 mm Hg. As the exocrine secretion was stimulated with sulphated cholecystokinin (CCK) octapeptide (American Peptide Company Inc., Sunnyvale Calif., USA) and secretin (American Peptide Company Inc.) in increasing doses, the pressure gradually rose to 15-20 mm Hg. This then stayed elevated, but towards the end of the experiment the pressure tended to fall to 11-13 mm Hg.

Example 4

Induction of Acute Pancreatitis

These set of experiments were designed to induce acute pancreatitis and were used as control studies. These were then compared to other experiments where with acute pancreatitis, Galanin or Galantide were given (see below).

Following experimental setup, the preparations were allowed to stabilise for 15 minutes. Then synthetic CCK and secretin (in saline containing 0.01% bovine serum albumin (Sigma Corporation, St Louis, Mo., USA) was administered as bolus injection (0.25-1.25 ml) via the femoral vein, at 30 minute intervals over 5 hours. The initial dose of CCK-secretin is 0.5 ug/kg. This was followed by increasing doses from 1 to 5 ug/kg. The final dose was given 5 hours after pancreatic duct ligation, and the experiment was terminated 3 hours later. At hourly intervals a blood sample (700 µl) was collected from the right femoral artery for analysis of the plasma levels of amylase and lipase. The first sample of blood is collected at the time of cannulation of the pancreatic duct. At the end of the experimental protocol the animal was euthanased with a lethal dose of sodium pentobarbitone (Lethabarb®, Arnolds of Reading, Baronia, Victoria, Australia). The pancreas was then harvested and fixed in 10% buffered formalin for subsequent histological examination and assessment of severity of pancreatitis.

Example 5

Galanin and Galantide Studies

The experiment setup and induction of acute pancreatitis was as described above. Several groups of animals were used depending on the drug administered and timing of infusion. Galanin or Galantide (American Peptide Company Inc.) was administered at the onset of acute pancreatitis (prophylactic), 2 or 3 hours after onset of acute pancreatitis (treatment).

a. Galanin was administered intravenously 15 minutes before pancreatic duct ligation as a bolus injection (0.5 nmol/kg), and then as an infusion (0.5 nmol/kg/15 min) after duct ligation for the duration of experiment.
b. Galantide was administered intravenously 15 minutes before pancreatic duct ligation as a bolus injection (1.5 nmol/kg), and then as an infusion (0.5 nmol/kg/15 min) after duct ligation for the duration of experiment.
c. Galantide was administered intravenously 2 hours post onset acute pancreatitis as a bolus (1.5 nmol/kg), and 15 minutes later as an infusion (0.5 nmol/kg/15 min) throughout the duration of experiment.
d. Galantide was administered intravenously 3 hours post onset acute pancreatitis as a bolus (1.5 nmol/kg), and 15 minutes later as an infusion (0.5 nmol/kg/15 min) throughout the duration of experiment.

The protocol c and d were included as they were thought to simulate the clinical situation.

Example 6

Plasma Amylase and Lipase Measurements

At hourly intervals, blood samples (700 µl) were collected in EDTA tubes from the right femoral artery for analysis of plasma amylase and lipase levels. The first sample was withdrawn just prior to pancreatic duct ligation and then at hourly interval till the end of the experiment. Blood samples were centrifuged at 2000 rpm for 5 minutes, the plasma collected and stored at −20° C. Amylase activity in plasma was assayed using an enzymatic colorimetric assay (AMYL kit, Roche/Hitachi, Mannheim Germany). Plasma lipase activity was determined using the Lipase-PSTM kit (Trinity, Biotech). Both assays were run on a centrifugal analyser (Cobas Bios, F Hoffmann-La Roche, Basle, Switzerland).

Example 7

Myeloperoxidase (MPO) Activity

MPO was extracted from frozen pancreata as described by Bhatia et al. (2000) *Gut* 47(6):838-844, and the activity determined by on the kinetic method of Bradley et al. (1982) *Journal of Investigative Dermatology* 78(3):206-9 run on a Cobas Bio instrument.

Example 8

Secretion Studies

Animals:

The possums were anaesthetized as described above. The left femoral vein was cannulated with two cannulae (1.05 mm OD, 0.35 ID) for administration of anaesthetic drugs and normal saline. The right femoral vein was also cannulated with a cannula (1.05 mm OD, 0.35 ID) for administration of galanin or galantide. A midline laparotomy was then performed. With minimal handling of tissues, the duodenum with the sphincter of Oddi was placed on a platform and stabilised with pins. The pancreatic duct component of the sphincter of Oddi was identified with the aid of a dissecting microscope and opened with micro-scissors. It was then cannulated (1.5 mm OD, 0.9 mm ID) advanced 4-5 mm and ligated with 5-0 prolene suture. This cannula was left open to collect pancreatic juice. After an initial stabilization period of 15 minutes, the pancreatic juice was collected every 30 minutes for 3.5 hours.

In separate groups of animals after the initial stabilization period galanin (0.5 nmol/kg bolus then 15 min later 2 nmol/kg/hr continuous infusion) or galantide (1.5 nmol/kg bolus then 15 min later 2 nmol/kg/hr continuous infusion) were administered.

Hyper-Stimulated Pancreatic Exocrine Secretion Study:

The experimental setup was similar to as described above. In the control group after an initial stabilization period of 15 minutes, the pancreatic juice was collected at half hourly intervals for one hour. This established the basal secretion rate. Then a mixture of cholecystokinin and secretin (CCK-SEC) was infused i.v at 5 µg (of each peptide)/kg/hr for the entire duration of the experiment.

The study groups received either galanin or galantide (doses as above) 1.5 hours after starting CCK-SEC infusion. The galanin or galantide infusion was continued for one and a half hour and then stopped. The CCK-SEC infusion was further continued for one hour. During the entire course of experiment, pancreatic juice was collected at half hourly intervals.

The quantity of the juice was measured and was then stored at −20° C. for subsequent assessments of amylase, lipase and total protein.

Study Groups:
Basal Secretion:

| Groups | N |
|---|---|
| Basal secretion (control group) | 5 |
| Galanin administration | 4 |
| Galantide administration | 4 |

Hyper-Stimulated Secretion:

| Groups | N |
|---|---|
| CCK-SEC (control group) | 4 |
| CCK-SEC + galanin administration | 4 |
| CCK-SEC + galantide administration | 4 |

Parameters Analyzed:

The quantity of pancreatic exocrine secretion was estimated gravimetrically (basal secretion and stimulated secretion).

The plasma amylase assay kit (Roche/Hitachi Mannheim, Germany) and lipase assay kit (Sigma, St. Louis, USA) were used in conjunction with Hitachi Autoanalyzer (Roche/Hitachi Mannheim) to estimate pancreatic juice amylase and lipase respectively.

Pancreatic exocrine protein secretion was estimated as follows. BSA saline (1 mg/ml) was used to generate the standard curve. Aliquots of 2, 4, 6, 8 and 10 µl were pipetted in the wells of microplate, in duplicate. Duplicate aliquots of pancreatic juice (usually diluted 1:300 with saline) were used. The total reaction volume was 200l which consisted of sample (80 µl), distilled water (80 µl) and BioRad Protein Assay Dye Reagent (40l). The absorbance was detected at 595 nm using a micro plate reader BIORAD model 680 (Biorad Lab, NSW, Pty, Ltd.).

All data are expressed as mean±standard error of mean of n number of animals.

Statistical Analysis

The data were analysed using ANOVA. If ANOVA indicated a significant difference, the data was further analysed using Student's t-test. Statistical significance was accepted at the $p<0.05$ level.

Mouse Studies

Female Balb C or Swiss mice weighing 15-32 grams were used for the acute pancreatitis experiments. Galanin knockout mice were used for acute pancreatitis studies and for molecular characterization of galanin receptors (galanin receptors 1, 2 and 3 (GalR1, GalR2 or GalR3)) mRNA expression. These mice were obtained from the Garvan Research Institute (Sydney, NSW, Australia). The galanin knockout mouse was developed by Wynick and colleagues. A 3.7 kb segment of the galanin locus, containing a functional galanin gene, exons 1-5, was removed and replaced with an artificial PGK-Neo cassette in reverse orientation. Galanin exons 1-5 contain the coding region for galanin and most of the galanin-associated peptide. After mutation, the new knockout gene was 4.9 kb shorter than the wild type galanin gene (Wynick et al. (1998) (1998). *Proceedings of the National Academy of Sciences of the United States of America* 95(21):12671-12676. Wild type littermates and Swiss mice were also used for molecular studies.

Studies were approved by the Animal Welfare Committee of the Flinders University.

A day before the experiment the animals were randomly assigned different cages as per the protocol of the experiment. All the animals were subjected to orbital bleeding after receiving intraperitoneal injections of ketamine hydrochloride (75 mg/kg; Ketamil Injection; Troy Laboratories Pty. Ltd., NSW, Australia) and medetomidine hydrochloride (0.3 mg/kg; Domitor, Orion Pharma, Novartis Animal Health Australasia Pty Ltd., New Zealand). Both ketamine and medetomidine were used as 10% solutions in the same syringe. All the animals then received an injection of atipamazole hydrochloride (1 mg/kg; Antisedan, Orion Pharma, Novartis Animal Health Australasia Pty Ltd., New Zealand) intraperitoneally, to reverse the effects of medetomidine. Atipamazole was also used as 10% solution. All animals were then fasted overnight with free access to water.

Induction of Acute Pancreatitis:

Two models have been used: a mild model (7 hourly caerulein injections) and a severe model (13 hourly caerulein injections) based on that originally described by Niederau et al. (1985) *Gastroenterology* 88(5 Pt 1); 1192-1204. The latter model has only been used for galantide studies to date. All the animals receive seven intraperitoneal (i.p.) injections of caerulein 50 µg/kg in 150 µl of 0.9% NaCl at hourly intervals over 6 hours. An analgesic agent, buprenorphine (0.1 mg/kg, Temgesic, Reckitt & Colman Products, Hull, distributed by Reckitt & Colman Pharmaceuticals NSW) was administered subcutaneously along with the first caerulein injection to provide analgesia for up to 12 hours. All the animals had free access to water during the course of experiment. Twelve hours after the first caerulein injection, the animals were euthanased by exsanguination.

Galanin, Galanin Antagonists (Galantide, M35, M40 and C7) Studies:

Acute pancreatitis was induced in mice as described above. With each caerulein injection, the animals were also given i.p. injections of galanin or galanin antagonist (American Peptide Company Inc., Sunnyvale Calif., USA). All the animals received analgesia as described above. The experiment was terminated twelve hours after the first injection by euthanasia of the mice. This same protocol was used with galanin-knockout and wild type littermates studies.

Control Groups:

In these sets of experiments, the animals received 7 intraperitoneal injections of saline, galanin or the individual galanin antagonist at hourly intervals over 6 hour duration. All the animals also received analgesia and the experiments were terminated twelve hours after the first injection as outlined above.

Doses of Galanin and Galanin Antagonists Used:

The doses of galanin and galanin antagonist were decided on the basis of experimental data generated in prior possum studies. Galanin was used in a dose 10 nmol/kg. Galantide was administered at 10 nmol/kg, 20 nmol/kg or 40 nmol/kg (in separate groups). M35, M40 and C7 were administered at 20 nmol/kg or 40 nmol/kg (in separate groups).

Blood and Tissue Collections and Analysis:

Mice were anesthetized by intraperitoneal injection of ketamine and medetomidine. All the animals were then subjected to orbital bleeding and blood was collected for subsequent estimation of plasma levels of amylase and lipase. Then the animals were euthanased by exsanguination. This was then followed by midline laparotomy. With minimal handling of tissues the pancreas was harvested and divided into two parts for myeloperoxidase (MPO) activity estimation and histological assessment of severity of pancreatitis.

The part of pancreas for MPO level estimation was weighed, frozen immediately and stored at −70° C. The part of pancreas for histological assessment was fixed in 10% buffered formalin overnight. These specimens were then embedded in paraffin blocks and 10 micron sections were cut and stained with haematoxylin and eosin. The slides were then examined by an independent, "blinded" and experienced pathologist. Modified Spormann scoring system was used to score each slide (Chen et al. (2000) *Gut* 47(4):539-545).

Biochemical Assays

Plasma amylase and lipase activity were measured as described in possums studies above.

MPO activity was extracted as described under possum studies and assayed using a kinetic assay run on a microtitre plate reader described by Moore-Olufemi et al. (2005) *Journal of Trauma-Injury Infection & Critical Care* 58(2):264-70 as follows. To duplicate 20 ul aliquots of each extract in microtitre plate wells, 100 ul of SureBlue Reserve reagent was added and gently mixed. The microtitre plate was then placed in a BIORAD model 680 (Biorad Lab, NSW, Pty, Ltd.) plate reader and the absorbance at 650 nm measure of a period of 2 minutes at room temperature. The reaction rates were calculated. Purified MPO from Calbiochem (La Jolla, Calif., USA) was used as positive control.

Experimental Groups (Mild Model):
Galanin and galantide studies (Normal mice):
1. Acute pancreatitis only (n=6).
2. Acute pancreatitis+galanin 10 nmol/kg (n=5).
3. Acute pancreatitis+galantide 10 nmol/kg (n=6).
4. Acute pancreatitis+galantide 20 nmol/kg (n=6).
5. Acute pancreatitis+galantide 40 nmol/kg (n=6).
6. Control group: saline+galanin 20 nmol/kg only (n=3).
7. Control group: saline+galantide 20 nmol/kg only (n=3).
8 Control group: saline+galantide 40 nmol/kg only (n=4).
9 Control group: saline+saline only (n=4)

Galanin and galantide studies (Galanin-knockout and wild type littermate mice):
1 Galanin-knockout+acute pancreatitis
2 wild type littermate+acute pancreatitis
3 Galanin-knockout+saline
4 wild type littermate+saline M35, M40, C7 Studies:
1 Acute pancreatitis only (n=8).
2 Acute pancreatitis+M35 20 nmol/kg (n=6).
3 Acute pancreatitis+M35 40 nmol/kg (n=6).
4 Acute pancreatitis+M40 20 nmol/kg (n=5).
5 Acute pancreatitis+M40 40 nmol/kg (n=5).
6 Acute pancreatitis+C7 20 nmol/kg (n=9).
7 Acute pancreatitis+C7 40 nmol/kg (n=9).
8 Control group: saline+M35 40 nmol/kg only (n=5).
9 Control group: saline+M40 40 nmol/kg only (n=5).
10 Control group: saline+C7 20 nmol/kg only (n=5).
11 Control group: saline+C7 40 nmol/kg only (n=6).

Galanin Receptor Immunohistochemistry:

Tissues (mouse pancreas, brain, colon—latter two are positive controls) were fixed in 10% buffered formalin and then processed using standard methods to embed in paraffin.

Sections (5 µm) were dewaxed in xylene (2 washes for 3 min each), rehydrated in 100% alcohol (2 washes for 3 min each) followed by water (2 washes for 3 min each). Endogenous peroxidase activity was blocked by washing sections in 0.3% hydrogen peroxide solution in phosphate buffered saline (PBS; 0.15 M NaCL in 0.01 M sodium phosphate, pH 7.3), followed by washing with PBS (2 washes for 5 min each). Preliminary studies found high temperature antigen retrieval was required for these antibodies. Slides were placed in target retrieval solution pH 9 (DakiCytomation, Glostrup, Denmark), bought to the boil using the microwave and then gently boiled for 10 mins at 10% power, then left in the solution to cool for 30 min. Sections were washed with PBS (2 washes for 5 min each). Sections were then placed in a humid box and 10% normal goat serum (Sigma-Aldrich, Castle Hill, NSW, Australia) in PBS was applied for 30 mins. The primary antibody (GalR1, GalR2 or GalR3; Alpha Diagnostics International, San Antonio, Tex., USA) was then applied in 10% normal goat serum in PBS and left in the humid box overnight at room temperature. Slides were washed with PBS (2 washes for 5 min) and EnVision+Dual Link System-HRP (DakoCytomation) was applied. Slides were washed again with PBS (2 washes for 5 min) and the liquid DAB substrate-chromagen (DakoCytomation) was applied for 5 min then washed with distilled water. The sections were counterstained with haematoxylin, dehydrated and coverslip-mounted with DePeX mounting medium (Gurr microscopy materials, BDH Chemicals).

Sections were viewed using an Olympus Bx50 microscope and images captured using the software program QCapture (QImaging, Burnaby, BC, Canada).

Example 9

Molecular Studies

Tissue Harvest:

Due to the high level of RNase in the pancreas, the pancreata were rapidly harvested to maximize the integrity of the RNA. The tissue was placed in a 2 ml Corning® tube and immediately frozen in liquid nitrogen. The frozen tissue was stored in a −80° C. freezer. The whole brain (a positive control) was harvested immediately after pancreas harvest and rapidly frozen as described above and stored in a −80° C. freezer.

RNA Extraction:

The various steps in this procedure were conducted on ice unless otherwise stated, to avoid degradation of RNA. The entire frozen pancreas or brain was ground to powder using a mortar with a pestle which had been pre-chilled with liquid nitrogen. Then 5 ml of ice-cold Trizol (Invitrogen, Carlsbad, USA) was added to the powdered pancreas (or 2 ml to the powdered brain) and mixed thoroughly with the pestle until the resulting paste was thawed to produce a Trizol lysate. A 200 µl aliquot of the pancreas (or 500 µl brain) Trizol lysate was pipetted into a 1.5 ml Eppendorf tube, and additional ice-cold Trizol was added to achieve a final volume of 1 ml. This mixture was then vigorously shaken to thoroughly mix the contents. The remaining Trizol lysate was aliquoted in 1.5 ml Eppendorf tubes and stored at −80° C.

The 1 ml of diluted Trizol lysate was incubated at room temperature for 5 minutes as described in the Trizol manufacturer's introduction. Then 200 µl of chloroform (Sigma Chemical Co, St Louis, USA) was added into the lysate and mixed well manually by vigorous shaking 10 times, and then incubated again at room temperature for 5 minutes. The phases were separated by centrifugation for 15 minutes at 12,000 g at 4° C. (Eppendorf Microfuge, 5414R, Germany). The aqueous (top) phase was transferred to a fresh tube (total volume approximately 500 µl). The organic phase was retained for genomic DNA extraction. Then 500 µl of room temperature isopropanol (Sigma) was added to the aqueous phase described above. The solution was shaken vigorously at least 10 times and incubated at room temperature for a further 10 minutes. The RNA precipitate was collected by centrifugation for 10 minutes at 12,000 g at 4° C. as above. This pellet was washed with 1 ml of room temperature 75% ethanol and mixed with a vortex mixer. The suspension was re-centrifuged at 7,600 g for 5 minutes at 4° C.

The RNA pellet was dissolved in ice-cold 100% formamide (Sigma) (20 µl). The concentration of RNA was determined using spectrophotometry by measuring the absorbance at 260 nm. The RNA was then diluted to 1 µg/µl in formamide (ice-cold).

DNAse I Treatment:

3 µg RNA (1 µg/µl in formamide) was precipitated by adding 7 µl of Ultra Pure Water (UPW) (Fisher Biotec, West Perth, Australia), 1 µl of 3M sodium acetate pH 5.2 and 25 µl of 100% ethanol. After 10 minute incubation on ice, the precipitate was collected by centrifugation at 12,000 g for 10 minutes at 4° C. The pellet was then washed in 200 µl of 75% ethanol, followed by centrifugation at 12,000 g for 10 minutes at 4° C. The pellet was dissolved in 15 µl of UPW. The DNase I digestion utilized the DNA-free™ kit (Ambion, Austin, USA). 10 µl of the RNA solution was treated with 1 µl of rDNase I (Ambion) and the addition of 1 µl 10× buffer (Ambion), mixed well and centrifuged. The mixture was incubated at 37° C. for 30 minutes in the PCR machine (Eppendorf, Mastercycler Gradient, Germany). The reaction was terminated by adding 2 µl of inactivation reagent (Ambion), followed by incubation at room temperature for 2 minutes, with occasional manual mixing. The solution was then centrifuged at 10,000 g for 90 seconds, followed by transfer of equal amounts into two fresh tubes.

Assessment of RNA Quality:

The quality of RNA, before and after DNase I treatment was determined by electrophoresis using a 1% agarose gel. For this purpose, electrophoresis was performed at 100V for 50 minutes in 0.045M Tris-Borate, 0.001M EDTA pH8 buffer. els were stained with 0.5 µg/ml ethidium bromide for 30 minutes and photographed with UV light exposure.

Reverse Transcription (RT):

RT of RNA was performed according to the instruction manual for SuperScript™ III (Invitrogen, Carlsbad, USA). In order to confirm a lack of contamination in the RT and real-time PCR reactions, each group of samples included a water control (no RNA sample) and each sample had a negative control (the same RT treatment without SuperScript™ III). Master mix I solution included 1 µl of random primers, 1 µl of 10 mM dNTP Mix (Invitrogen) and 11 µl sterile UPW for each reaction (total 13 µl mixture for each reaction).

Master mix II solution consisted of 4 µl 5× First-Strand Buffer (Invitrogen), 1 µl 0.1 M DTT, 1 µl RNaseOUT™ Recombinant RNase Inhibitor (Invitrogen) and 1 µl of SuperScript™ III RT (200 units/µl) (Invitrogen) for each reaction. Master mix II for reverse transcriptase negative controls contains the same reagents except UPW was substituted for SuperScript™ III.

For each RNA sample (5 µl) (experimental, negative reverse transcriptase controls and water controls), 13 µl of Master mix I was added. The mixture was heated at 65° C. for 5 minutes in the PCR machine and incubated on ice for at least 1 minute. 7 µl of the appropriate Master mix II solution was added to the corresponding samples, followed by mixing and incubation at 25° C. for 5 minutes. Further incubation in the PCR machine was performed at 50° C. for 60 minutes and then the reaction was terminated by heating at 70° C. for 15 minutes. The cDNA was diluted in 200 µl of UPW and was then ready for PCR.

Primer Design:

Oligonucleotide primers for beta-actin, hypoxanthine-guanine phosphoribosyl transferase (HPRT), porphobilinogen deaminase (PBGD), Gal, GalR1, GalR2 and GalR3 were designed using Primer 3 (Primer 3, 2004). Primer specificity was confirmed using BLAST (Mega Blast, 2006), with primers as the query sequence and *mus musculus* as the organism. The sequences of the 18s ribosomal RNA (rRNA) primers were provided by Brenton Reynolds (Flinders Medical Centre). The primer sequences are listed in the Table.

| Primer | Sequence |
|---|---|
| Gal f | ACTGTGCACGTGTGTCCTG (SEQ ID NO: 1) |
| Gal r | CAGCTTCAAAGCAGAGAACAGC (SEQ ID NO: 2) |
| GalR1 f | GGCAGCTTATTCTCCACAGC (SEQ ID NO: 3) |
| GalR1 r | TGATCTTCAGTAGACCCACGAG (SEQ ID NO: 4) |
| GalR2 f | CAGATTGCGAGAGTGGTGACATAG (SEQ ID NO: 5) |
| GalR2 r | CGGACAGGGTTAGTCTAGTC (SEQ ID NO: 6) |
| GalR3 f | ACCACCACCGCCTTCATC (SEQ ID NO: 7) |
| GalR3 r | TTGCTGACAGGATGCAGAAG (SEQ ID NO: 8) |
| Beta-actin f | ACCGATCCACACAGAGTACT (SEQ ID NO: 9) |
| Beta-actin r | GGATCTCAGGTAGTTCAAGGACTCC (SEQ ID NO: 10) | f = forward; r = reverse

Extraction of Genomic DNA from Trizol:

After RNA extraction the red organic phase of the Trizol lysate contained genomic DNA and protein. 300 µl of 100% ethanol was added to the organic phase, mixed and stored at room temperature for 4 minutes. DNA was precipitated by centrifugation at 2,000 g for 5 minutes at 4° C. The DNA pellet was then washed 3 times for 30 minutes each in 1 ml of a 0.1 M sodium citrate buffer pH 8.5 in 10% ethanol. These washes were performed on a suspension mixer at room temperature. A further 2 washes were performed in 1.5 ml 75% ethanol for 20 minutes each at room temperature. After centrifugation at 2,000 g for 5 minutes at 4° C., the supernatant was removed, the DNA pellet was dried briefly and then dissolved in 8 mM NaOH (200 µl for brain & 50 µl for pancreas). Insoluble solids were removed by centrifugation at 12,000 g for 10 minutes at 4° C. The pH of the supernatant was adjusted to 8.0 using HEPES buffer.

Real-Time RT-PCR:

All RT-PCR experiments were performed using Quantitect™ 2×SYBR® Green master mix supplied by QIAGEN (Hilden, Germany) in 0.1 ml reaction tubes and a 72 well rotor. The reaction volume was 20 µl, containing 10 µl of Quantitect™, 2 µl of 5 µM forward primer, 2 µl of 5 µM reverse primer and 6 µl of cDNA. A master mix was firstly made by mixing all the reagents in a 1.5 ml Eppendorf tube except cDNA, then 14 µl of the master mix was added to each reaction tube. 6 µl of cDNA was added last. The experimental sample and positive control were cDNA from pancreas and brain respectively. The negative control included cDNA through RT without RNA and an UPW sample. For each experimental sample, positive or negative control, triplicate samples were subjected to real time PCR.

All PCRs were performed in a RotorGene 3000 (Corbett Research, Sydney, Australia) under the following conditions:
  95° C. for 15 minutes
  Cycling for 45 cycles: 95° C. for 20 seconds, various annealing temperatures for primers, as listed in Table 2.1 for 20 seconds, 72° C. for 20 seconds
  Hold at 72° C. for 4 minutes for final extension
  Melt from 60° C. to 99° C., rising 0.5 degrees for each step, waiting for 5 seconds on the first step and 5 seconds for each subsequent step
  All fluorescence acquisition was acquired to the SYBR green channel PCR Product Verification:

The PCR products were firstly separated on the basis of size using 3% agarose gel electrophoresis. For this purpose, electrophoresis was performed at 180V for 50 minutes in 0.5×TBE buffer and the molecular weights of each product were calculated based on the standard pUC19/HpaII (Geneworks, Adelaide, Australia). Gels were stained with 0.5 µg/ml ethidium bromide for 30 minutes and photographed during UV light exposure for analysis. PCR products for sequencing were prepared by Dr Damian Hussey (Dept Surgery, Flinders Medical Centre), and sequenced at the Southpath and Flinders Sequencing Facility.

Amplification Efficiency:

Amplification efficiency (AE) is the measurement of fold amplification per PCR cycle. The AE of each gene was calculated using the take-off cycle (Ct) slope method (Applied Biosynthesis, 2005). A two-fold dilution series of the target DNA was first generated (amount of DNA for each PCR reaction=10 ng, 5 ng, 2.5 ng, 1.25 ng, 0.625 ng, 0.3125 ng or 0.15625 ng). Ct value for each dilution was determined by PCR. A plot of average Ct versus log DNA amount was then constructed. $AE=e^{(-1/-m)}$, where m is the slope of the curve.

Comparative concentration of each gene was determined from Ct by the formula:

$$\text{Comparative concentration} = AE^{(Reference\ Ct - Sample\ Ct)}$$

Reference Ct was set as the first take-off for the normal pancreas. Sample Ct was the take-off for any sample of interest.

Normalisation was achieved by dividing the relative concentration of a gene of interest by the mean relative concentration of the housekeeping gene for the same sample. This determines the change in the expression of the gene of interest relative to the change in constitutive expression, which establishes the actual effect of treatment upon gene expression. This method was used to compare the same gene or different genes that had the same AE in different samples.

Due to the differential amplification efficiencies of different genes, quantitative comparison is not valid using only the concentration normalisation method described. In this situation, another comparison method, normalisation using the sample Ct to calculate the gene copy number present in the cDNA sample, was used. The amount of cDNA used in the real-time PCR can be calculated using the standard DNA dilution curve (Ct vs log the amount DNA used for PCR) and the Ct data from the cDNA sample. Preliminary experiments indicated that 18s rRNA was a satisfactory house keeping gene for analysing and normalising gene expression in the pancreas. It should be noted that normalisation using 18s rRNA expression is essentially the same as normalisation using the amount of total RNA, because ribosomal RNA constitutes approximately 95% of total RNA.

Western Blots Sodium Dodecyl Sulphate-polyacrylamide Gel (SDS-PAGE) Electrophoresis:

Pancreata and brains were harvested from euthanased wild type Swiss mice as described above, snap frozen in liquid nitrogen and stored in a −80° C. freezer. Whole frozen pancreas or brain was homogenized in 2 ml or 5 ml of homogenization buffer respectively (Dufourny, L. and Skinner, D.C. (2005) *Brain Res.* 1054(1):73-81) using a pre-chilled mortar and pestle. The homogenate was transferred to a 1.5 ml Eppendorf tube and further homogenized with an electric pestle (Dremel, Racine, Wis., USA). The homogenate was incubated on ice for 30 minutes and then centrifugation at 2000 g for 10 minutes at 4° C. The supernatant, containing total protein extracted from tissue, was then transferred to a fresh tube. Due to previous difficulties with band detection on Western blots, a membrane protein enriched fraction was prepared to increase the concentration of galanin receptor protein for SDS-PAGE. The supernatant from the centrifugation step described above was re-centrifuged at 100,000 g for 1 hour at 4° C., resulting in a membrane protein pellet. The pellet was then dissolved in the original homogenization buffer.

Protein Assay:

The Bio-Rad protein assay was used to estimate the protein concentration. Bovine serum albumin (BSA) (Sigma) was used to construct a standard curve. The absorbance of known concentrations of BSA were measured using a microplate reader (Bio-Rad, Model 680, Japan) at a wavelength of 595 nm. Aliquots of homogenate (100 μl) were precipitated with 500 μl ice cold 5% trichloroacetic acid (TCA) solution, incubated on ice for 10 minutes, centrifuged at 10,000 g for 2 minutes. The pellet was then dissolved in 100 μl of PBS buffer and triplicate aliquots used in the Bio-Rad protein assay. The concentrations of the protein in these samples were estimated using the standard curve generated.

SDS-PAGE:

The membrane protein fraction was denatured in an equal volume of sample/reducing buffer (Appendix) at 99° C. for 10 minutes in the PCR machine.

300 μg of total protein or membrane protein enriched fraction was loaded onto a 10% SDS-PAGE gel. The 10% separating gel (length 10 cm, width 5 cm, thickness 0.2 cm) was prepared by combining 5.2 ml separating gel buffer (Appendix), 9.8 ml distilled water, 5 ml 30% polyacrylamide and degassed for 5 min. Then 34 μl N, N, N', N'-tetramethylethylenediamine (TEMED) (Bio-Rad) was added immediately prior to use along with 74 μl of freshly made 10% ammonium persulphate (Bio-Rad). The contents of the separating gel were mixed well, and poured between the two glass plates. On the top of the separating gel, a 4% stacking gel was poured. The stacking gel was prepared by mixing 1.755 ml stacking gel buffer stock (Appendix), 4.32 ml distilled water, 0.675 ml 30% polyacrylamide (Bio-Rad), 34 μl TEMED and then 74 μl of freshly made 10% ammonium persulphate. The gel was run for 15 minutes at 10 mA, followed by 50 minutes at 20 mA.

Silver Stain:

The gel was fixed in fixing solution (Appendix) for 30 minutes at room temperature, and then transferred to incubation solution (Appendix) for 10 minutes, followed by 2 water washes of 5 minutes each, with shaking. After incubating for 30 minutes in silver solution (Appendix), the gel was placed in developing solution (Appendix). Stop solution (EDTA) (Appendix) was used to stop colour development. The gel was stored in 10% glycerol in water before photography.

Western Blot:

Samples for Western blot were treated identically to samples prepared for SDS-PAGE, with respect to tissue harvesting, homogenization, determination of protein concentration, protein denaturation and SDS-PAGE but not silver stained. The protein bands on the gel were transferred to nitrocellulose membrane (Amersham, Buckinghamshire, UK) at OOV for at least 1 hour. The gel was then silver stained to assess the efficiency of the transfer. A blank gel indicated that protein transfer to the membrane was complete. The transfer membrane was blocked in 3% Blotto (Appendix), with shaking, for 1 hour at room temperature, then overnight at 4° C. Transfer membranes were incubated in the corresponding primary antibody (Anti-Mouse GalR1 antibody, Anti-Mouse GALR2 antibody, Anti-Mouse GALR3 antibody, (Alpha Diagnostic, San Antonio, Tex., USA)) each at a 1:1000 dilution in PBS buffer with shaking for 1 hour at room temperature, followed by overnight incubation at 4° C. The membranes underwent 3×10-minute washes in TBS buffer (PBS buffer+0.05% Tween 20) at room temperature. Anti-rabbit IgG-HRP (Sigma) was used at a dilution of 1:2000 in PBS buffer for 2 hours at room temperature. Each membrane underwent 3×15-minute washes in TBS at room temperature.

Enhanced Chemiluminescence Detection:

Solution A and solution B (Amersham) were freshly prepared and mixed to produce the detection solution. The membrane was placed in the detection solution for 1 minute and exposed to the film for approximately 5 minutes before being transferred to a film developer.

Example 10

Results

Molecular studies were undertaken in mice to establish the relative expression of the 3 known galanin receptors (galanin receptor 1, 2 and 3 (GalR1, GalR2, GalR3)).

FIG. 1 shows PCR detection of mRNA for all 3 galanin receptor subtypes in the mouse pancreas. In wild type mice, GalR1 was very poorly expressed whereas GalR3 is the most abundant with GalR2 expression being intermediate. A similar profile was observed with galanin receptors in the galanin knockout mouse, although the relative expression of the 3 receptors was reduced.

Figure 2:
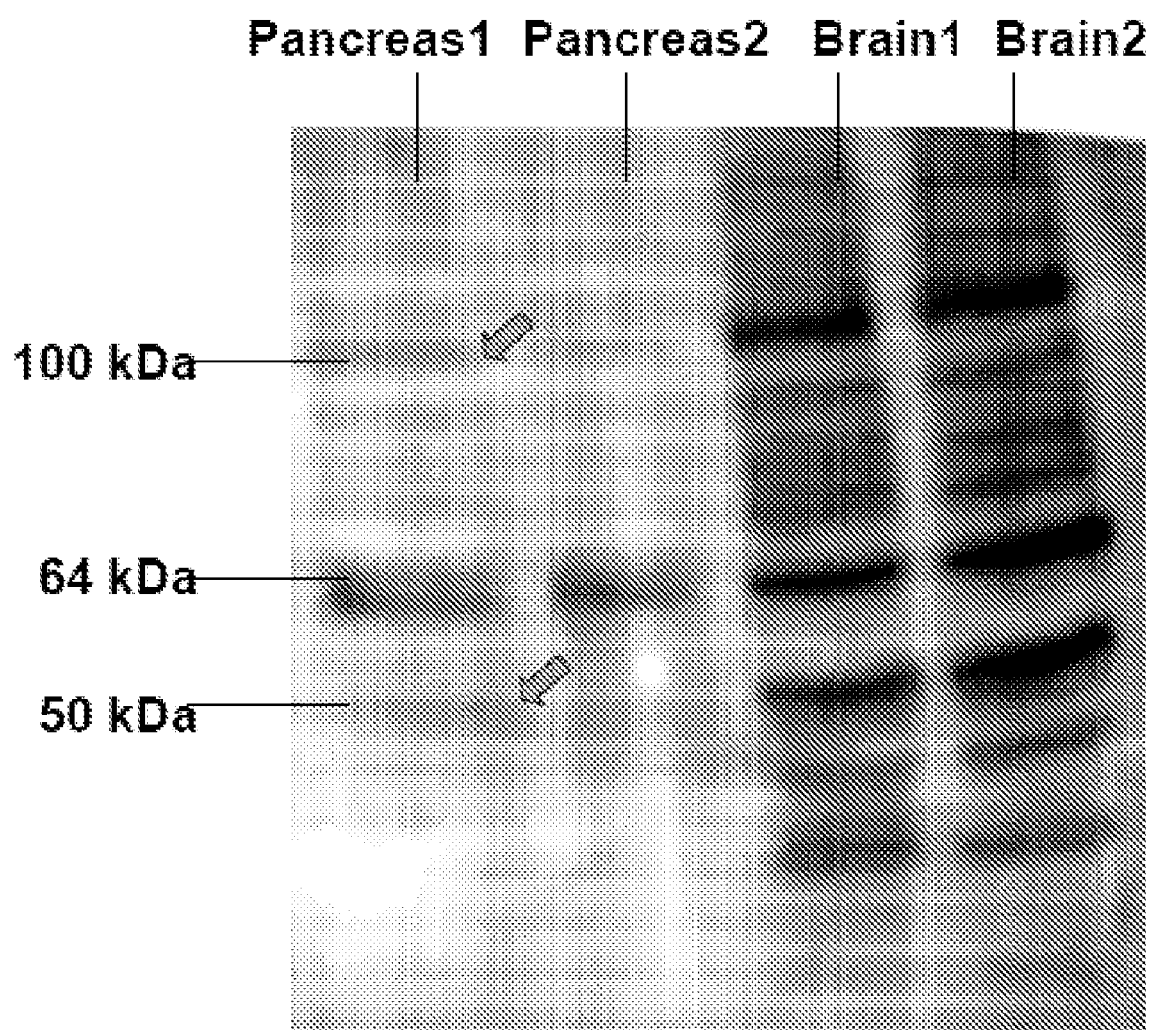
FIG. 2 shows Western blot analysis of mouse pancreatic GalR 1. The image shows Western blot of mouse pancreatic protein extract run on SDS-PAGE gel electrophoresis. GalR 1 antisera from Alpha Diagnostics was used and shows the predicted 47.4 kDa band and a band corresponding to the reported dimer (arrows). Other bands are evident which may represent posttranslational products, degradation products and/or non specific binding. Brain tissue was used as a positive control.
Figure 3:
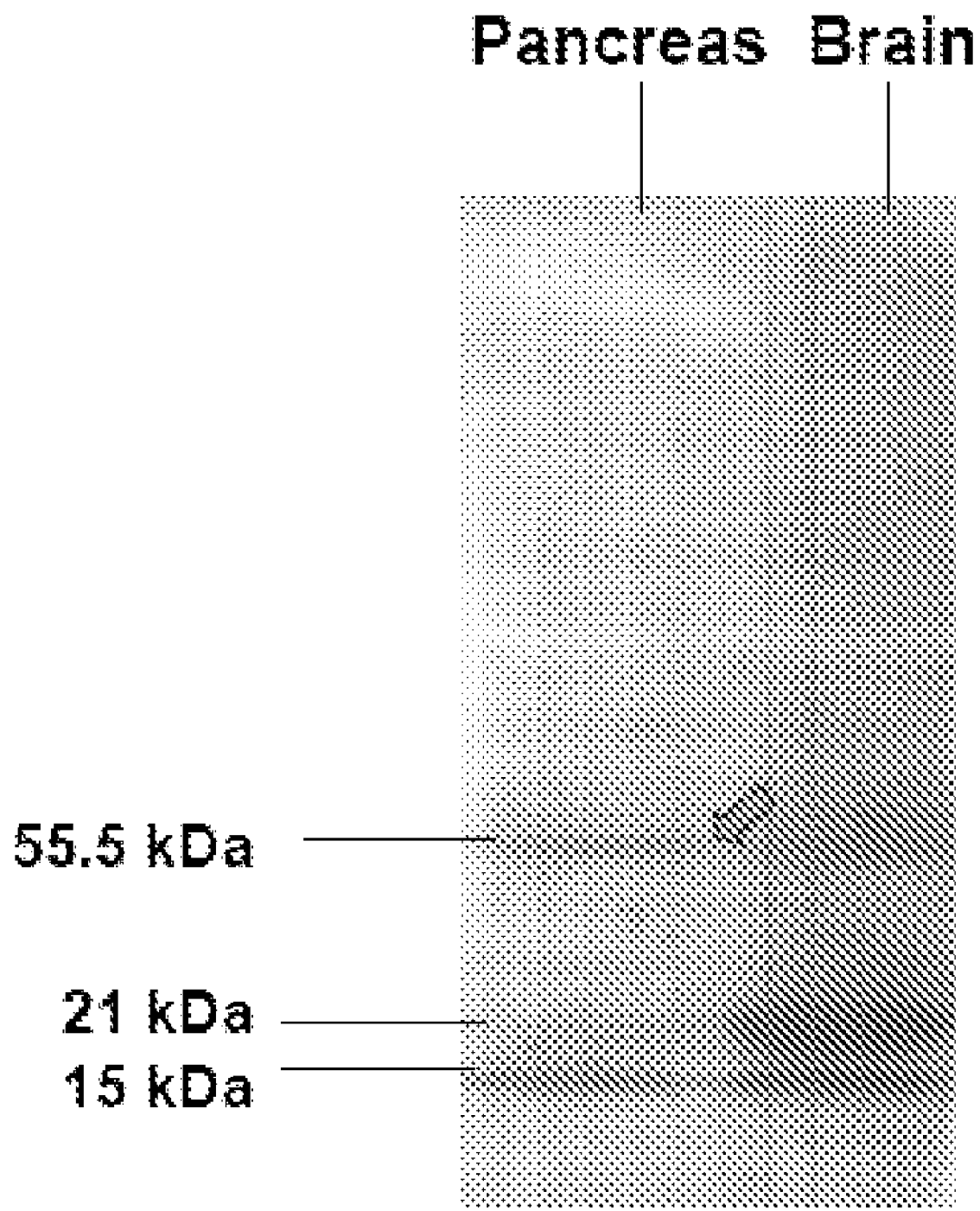
FIG. 3 shows Western blot analysis of mouse pancreatic GalR 2. The image shows the Western blot of mouse pancreatic protein extract run on SDS-PAGE gel electrophoresis. GalR 2 antisera from Alpha Diagnostics was used and shows the predicted 55.8 kDa band (arrow). Other bands are evident which may represent posttranslational products, degradation products and/or non specific binding. Brain tissue was used as a positive control.
Figure 4:
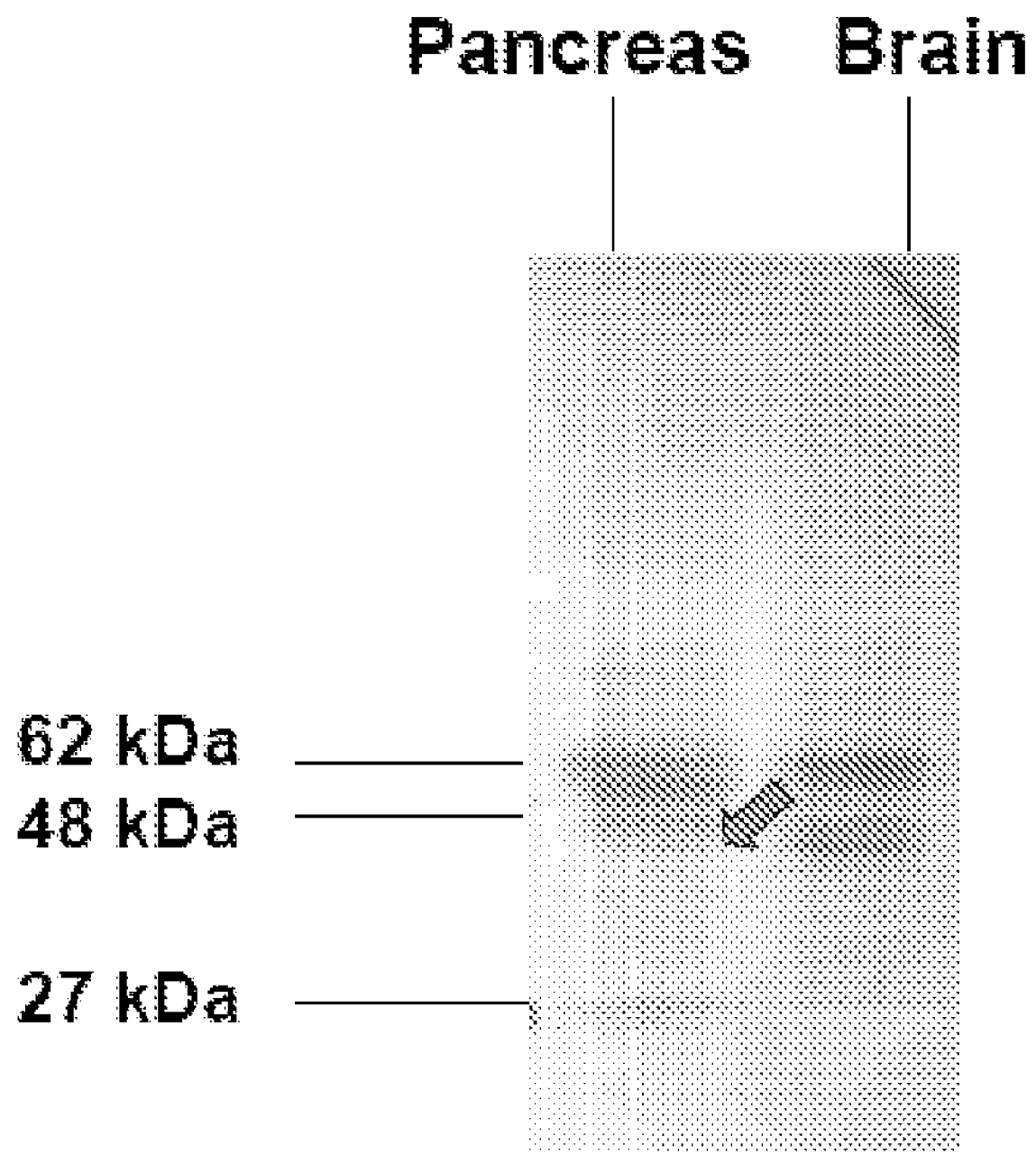
FIG. 4 shows Western blot analysis of mouse pancreatic GalR 3. The image shows the Western blot of mouse pancreatic protein extract run on SDS-PAGE gel electrophoresis. GalR 3 antisera from Alpha Diagnostics was used and shows the predicted 45.7 kDa band (arrow). Other bands are evident which may represent posttranslational products, degradation products and/or non specific binding. Brain tissue was used as a positive control.

Western blot analysis revealed that all three galanin receptor proteins were present in the mouse pancreas at the expected molecular weight (FIGS. 2 to 4). Additional bands reflecting possible posttranslational modification, degradation products and non-specific binding were also observed but further studies are required for clarification.

Figure 5:
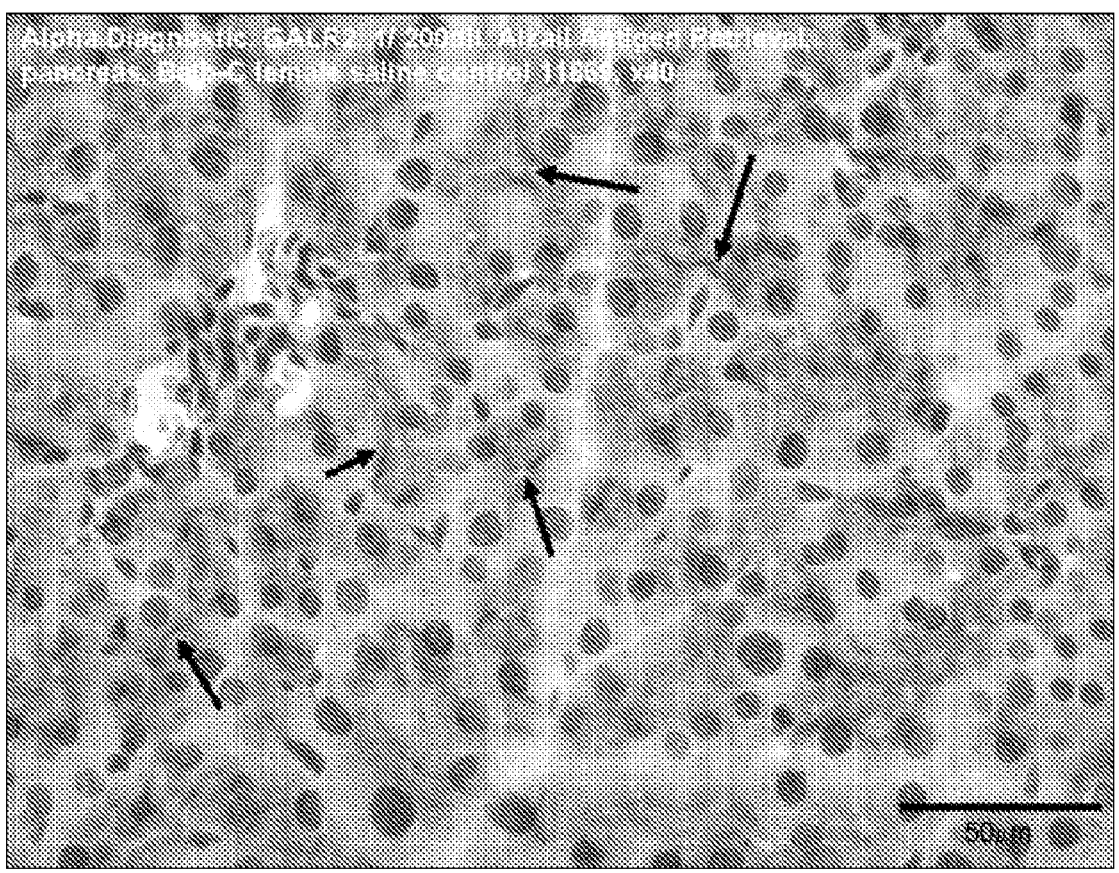
FIG. 5 shows GalR 2 immunohistochemical distribution in the mouse exocrine pancreas. The image depicts immunohistochemical staining for GalR 2 and shows staining of the basal cytoplasm and membrane of some acinar cells (arrows). Antisera from Alpha Diagnostics.
Figure 6:
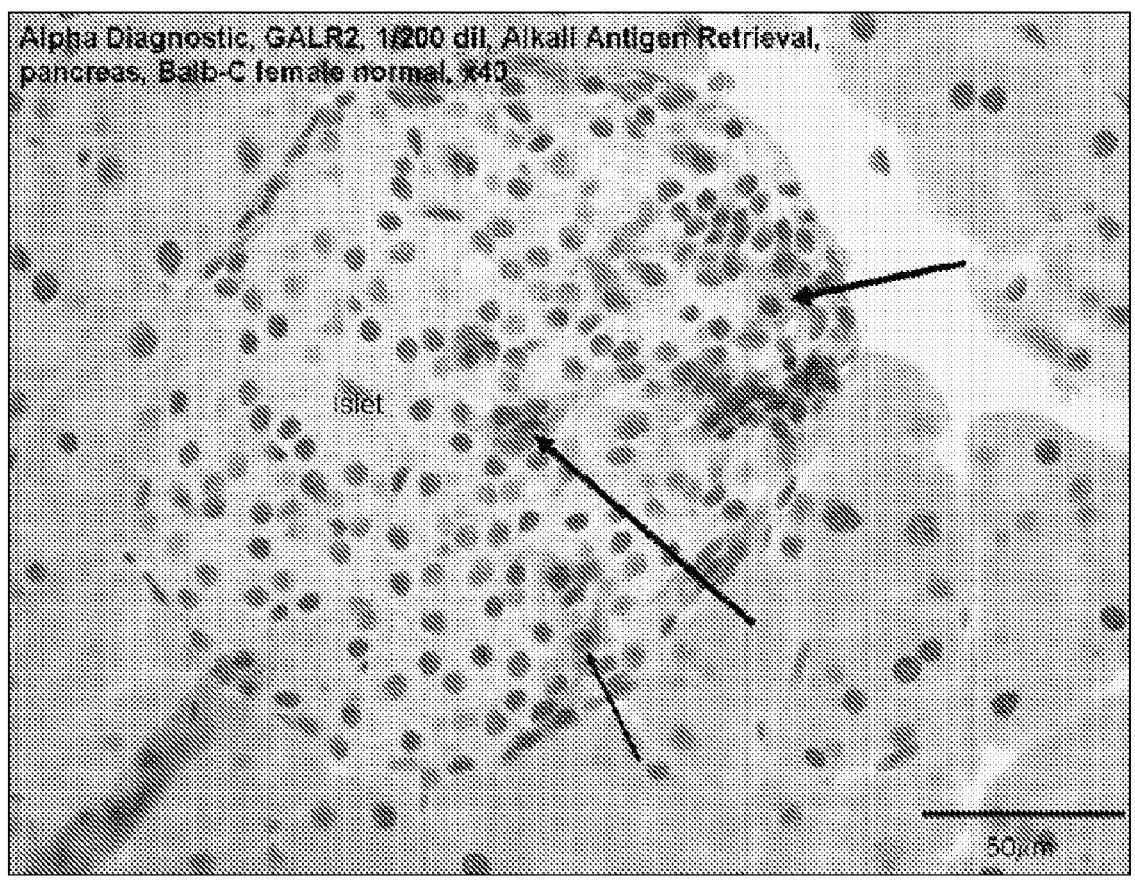
FIG. 6 shows GalR 2 immunohistochemical distribution in the mouse endocrine pancreas. GalR 2 staining appears to be localised in blood vessels or nerves in the pancreatic islets (arrows). Antisera from Alpha Diagnostics.

Immunohistochemical localisation of receptors had begun with a focus on galR2 and 3. Preliminary studies with commercially available antisera has so far revealed little labelling for GalR3. FIGS. 5 and 6 illustrate GalR2 labelling in acini and islet in the mouse pancreas. GalR2 staining of the basal cytoplasm and membrane of some acinar cells (arrows) are depicted in FIG. 5. GalR2 also appears to be localized in blood vessels or nerves in the pancreatic islets (FIG. 6; arrows).

Example 11

Pancreatitis Studies

Possum

Figure 7:
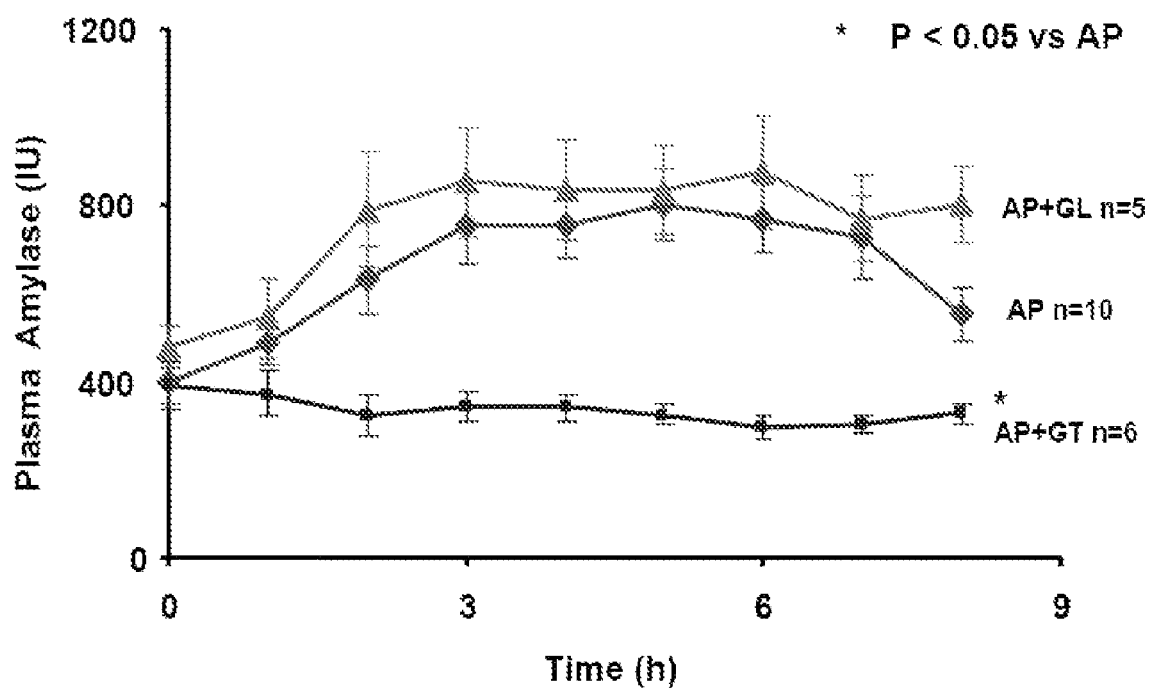
FIG. 7 shows plasma amylase activity increased as a function of time in a possum model of AP, peaking at about 2 hours, remaining at this level until 7 hours and then declined. This profile was unaffected by administration of GL (0.5 nmol/kg bolus followed by 2 nmol/kg/h continuous i.v. infusion for the duration of experiment) which was initiated 15 minutes prior to AP induction. In contrast, administration of GT (1.5 nmol/kg bolus followed by 2 nmol/kg/h continuous i.v. infusion for the duration of experiment) which was initiated 15 minutes prior to AP induction completely suppressed the AP-induced rise in plasma amylase activity ($P<0.05$).
Figure 8:
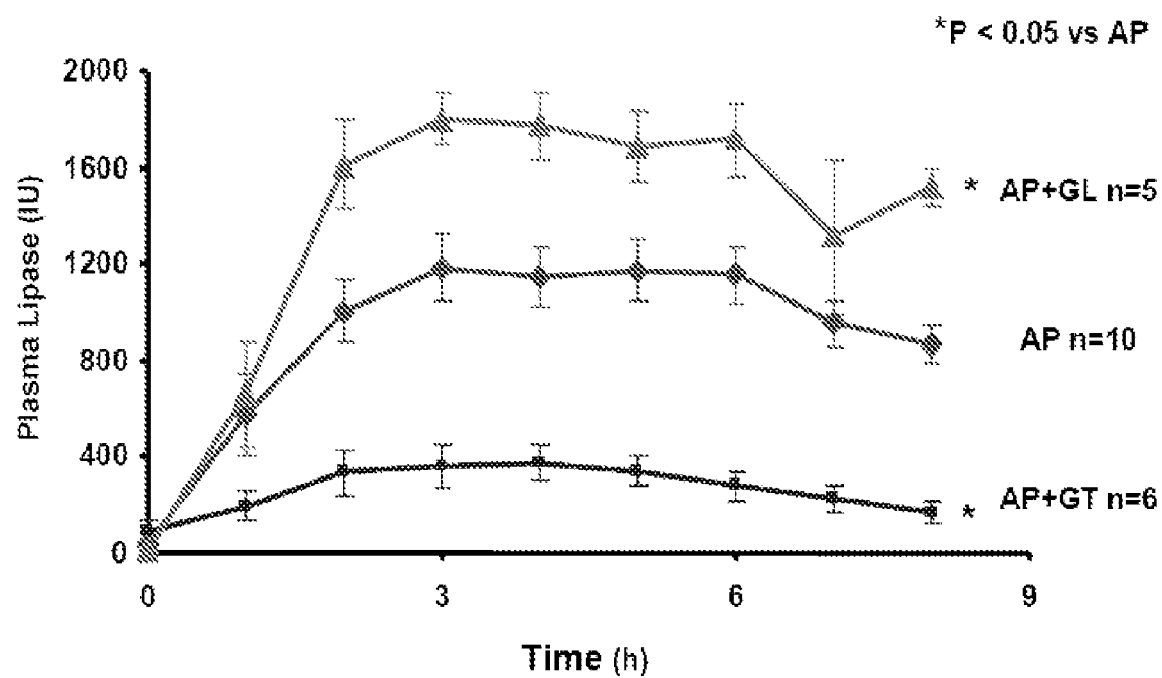
FIG. 8 shows plasma lipase activity as a function of time in a possum model of acute pancreatitis (AP) with and without administration of galanin (GL) or galantide (GT). Plasma lipase activity increased as a function of time in a possum model of AP, peaking at about 2 hours, remaining at this level until 6 hours and then declined. The plasma lipase level increased following the administration of GL (0.5 nmol/kg bolus followed by 2 nmol/kg/h continuous i.v. infusion for the duration of experiment) which was initiated 15 minutes prior to AP induction ($P<0.05$). In contrast, administration of GT (1.5 nmol/kg bolus followed by 2 nmol/kg/h continuous i.v. infusion for the duration of experiment) which was initiated 15 minutes prior to AP induction markedly suppressed the AP-induced rise in plasma lipase activity ($P<0.05$).
Figure 9:
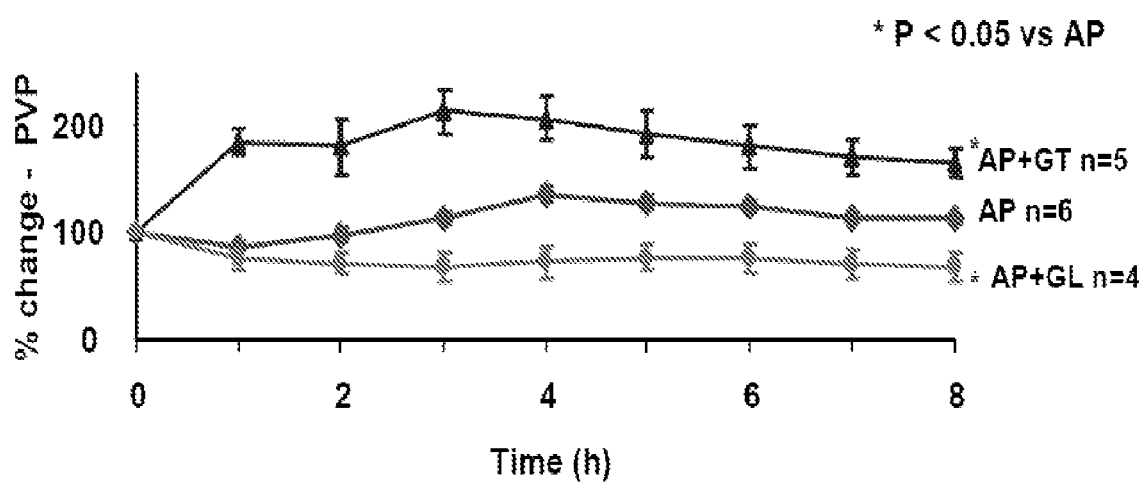
FIG. 9 shows PVP as a function of time in a possum model of acute pancreatitis (AP) with and without administration of galanin (GL) or galantide (GT). PVP displayed a biphasic profile as a function of time in a possum model of AP. A modest fall in PVP was the initial phase which recovered to baseline at 2 hours and then increased, peaking at 4 hours and then gradually declining to baseline by 7 hours post-AP induction. This profile was changed to a sustained increase in PVP by the administration of GL (0.5 nmol/kg bolus followed by 2 nmol/kg/h continuous i.v. infusion for the duration of experiment) which was initiated 15 minutes prior to AP induction ($P<0.05$). In contrast, administration of GT (1.5 nmol/kg bolus followed by 2 nmol/kg/h continuous i.v. infusion for the duration of experiment) which was initiated 15 minutes prior to AP induction produced a sustained fall in PVP for the duration of the experimental period ($P<0.05$).
Figure 10:
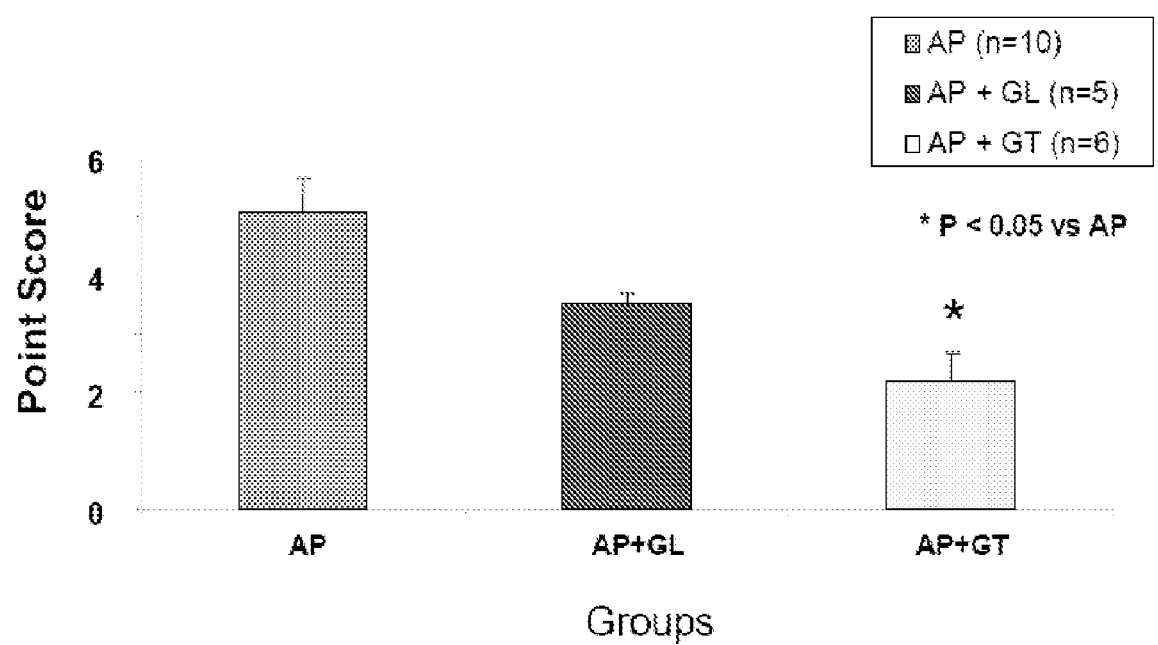
FIG. 10 shows pancreatic oedema in a possum model of acute pancreatitis (AP) with and without administration of galanin (GL) or galantide (GT). Possum pancreas was harvested at 8 hours post-AP induction from animals used the studies described in the previous figures, fixed in formalin and processed for standard H&E histology. Oedema was assessed using a point counting method. As expected, AP induced pancreatic oedema which was significantly decreased by GT ($P<0.05$) but not GL treatment.

The effect of treatment with galanin or galantide (15 minutes prior to the pancreatitis onset) in the possum model of acute pancreatitis are illustrated in FIGS. 7 to 12. FIG. 7 shows that administration of galanin did not alter the time-course of the pancreatitis-induced hyperamylasemia. In contrast, galantide administration completed prevented the pancreatitis-induced increase in plasma amylase. FIG. 8 shows that administration of galanin exacerbated the pancreatitis-induced hyperlipasemia. In contrast, galantide administration markedly depressed the pancreatitis-induced increase in plasma lipase. FIG. 9 shows that acute pancreatitis produces a biphasic change I pancreatic vascular perfusion (PVP), characterised by an initial small fall, then an increase in PVP with return to baseline values by 7-8 hours. Galanin treatment depressed the PVP for the duration of the experiments whereas galantide treatment increases PVP from the outset and this change is sustained for the duration of the experiment. Reduced PVP is conducive to necrosis. FIG. 10 demonstrates that pancreatic oedema, the major pancreatic change in this model of acute pancreatitis, was reduced with galantide treatment.

Figure 11:
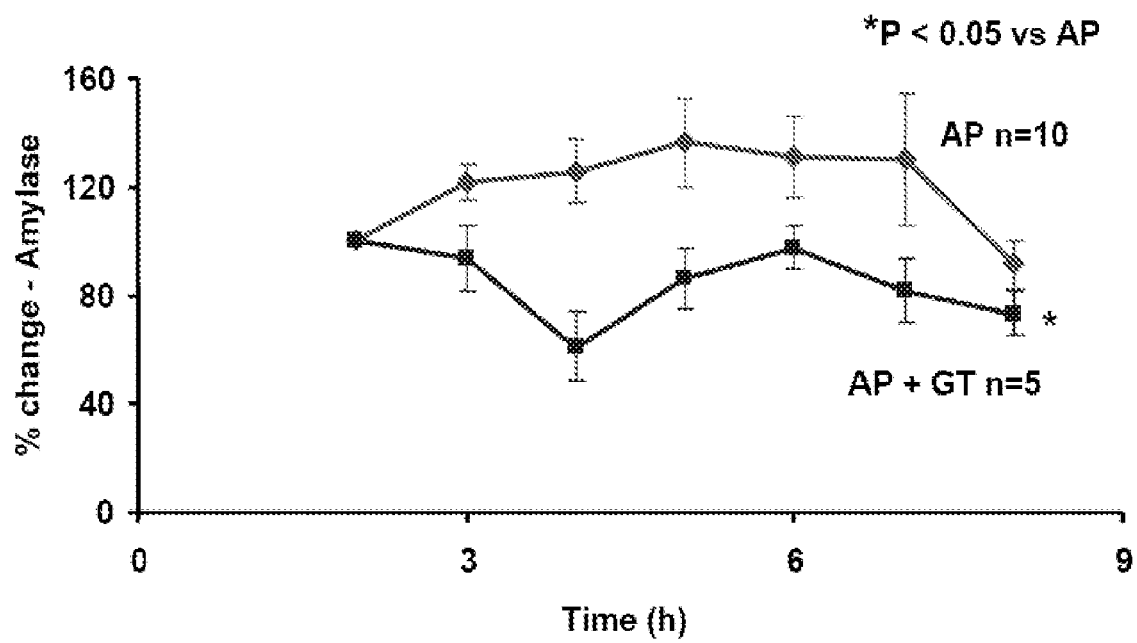
FIG. 11 shows plasma amylase activity as a function of time in a possum model of acute pancreatitis (AP) with and without delayed (2 hour) administration of galantide (GT). Plasma amylase activity increased as a function of time in a possum model of AP peaking at about 2 hours, remaining at this level until 7 hours and then declined. The administration of GT (1.5 nmol/kg bolus followed by 2 nmol/kg/h continuous i.v. infusion for the duration of experiment) which was initiated at 2 hours post-AP induction reduced the AP-induced rise in plasma amylase activity ($P<0.05$).
Figure 12:
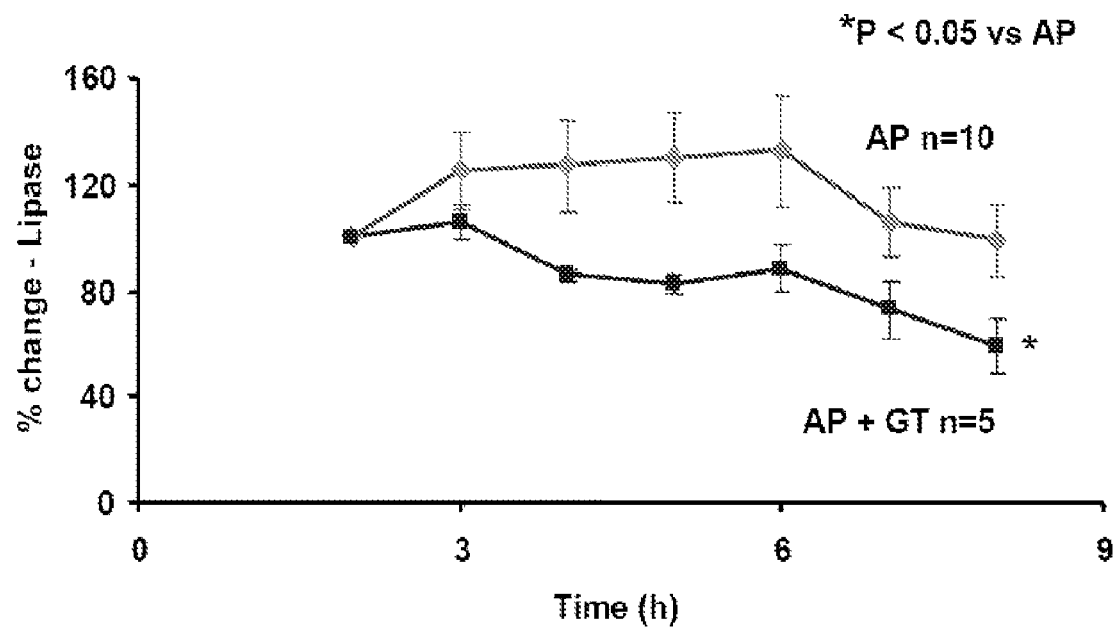
FIG. 12 shows Plasma Lipase activity as a function of time in a possum model of acute pancreatitis (AP) with and without delayed (2 hour) administration of galantide (GT). Plasma amylase activity increased as a function of time in a possum model of AP, peaking at about 2 hour, remaining at this level until 7 hours and then declined. The administration of GT (1.5 nmol/kg bolus followed by 2 nmol/kg/h continuous i.v. infusion for the duration of experiment) which was initiated at 2 hours post-AP induction suppressed the AP-induced rise in plasma lipase activity ($P<0.05$).

The effect of delaying galantide administration by 2 hours after the onset of pancreatitis (roughly equivalent to human patient arrival in emergency) on hyperenzymemia is shown in FIGS. 11 and 12. FIGS. 11 & 12 demonstrate that administration of galantide 2 hours after ductal ligation in possums reduces plasma amylase and lipase secretion.

In summary, these data show that administration of galantide prior to the onset and also after onset of acute pancreatitis in possums reduces the severity of pancreatitis.

Figure 13:
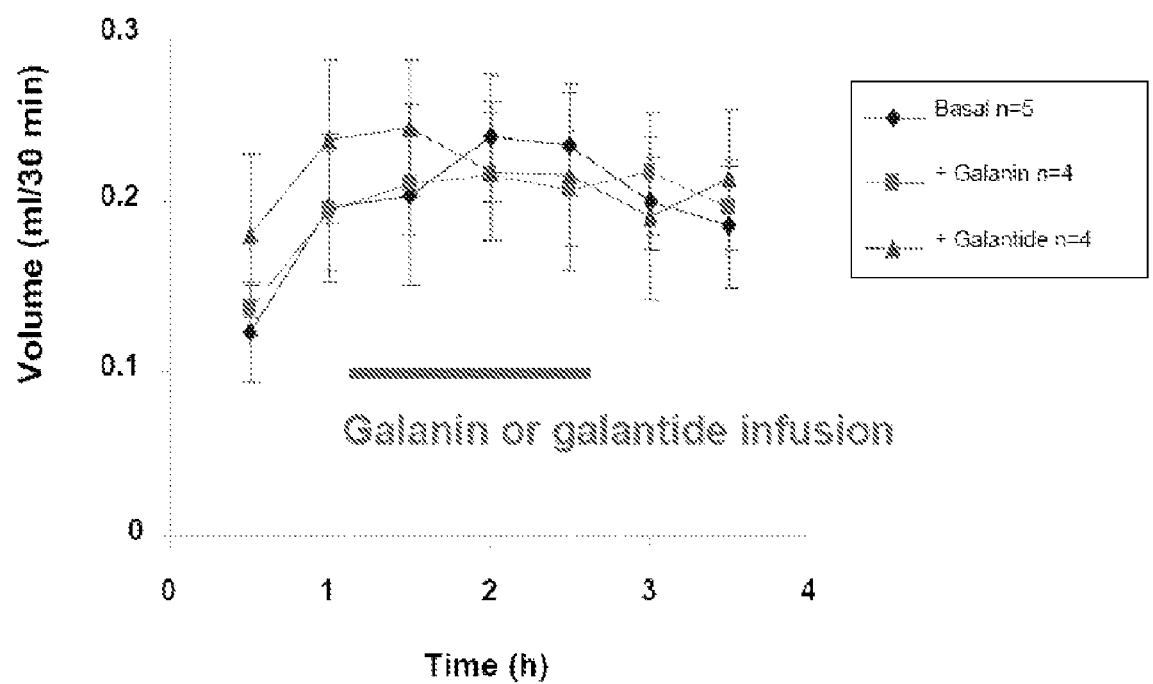
FIG. 13 shows Basal pancreatic exocrine secretion in anaesthetised possums with and without galanin or galantide treatment. In a preliminary study to determine if galanin or galantide treatment influences basal pancreatic exocrine secretion, pancreatic juice was collected at 30-minute intervals from anaesthetised possums. Galanin or galantide were administered at 1 hour (dose and route as described in previous figure legends) for a 2 hour period. Neither agent altered the basal rate of exocrine secretion.
Figure 14:
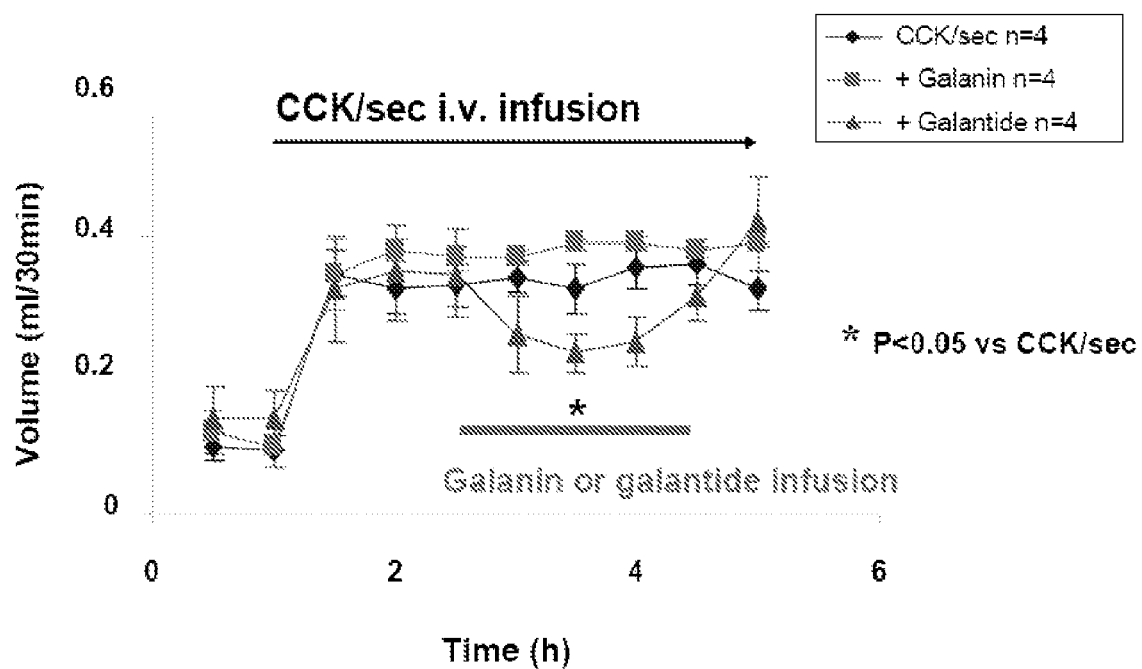
FIG. 14 shows hyperstimulated pancreatic exocrine secretion in anaesthetised possums with and without galanin or galantide treatment. In a preliminary study to determine if galanin or galantide treatment influences hyperstimulated pancreatic exocrine secretion (as in the possum acute pancreatitis model), pancreatic juice was collected at 30-minute intervals from anaesthetised possums. Cholecystokinin and secretin (CCK/sec) were co-administered as a continuous i.v. infusion (5 ug/kg of each/hour) commencing at 1 hour. Galanin or galantide were administered at 2 hours as described in previous figure legends for a 2-hour period. Hyperstimulation resulted in a sustained elevation in the volume of pancreatic juice secreted which was decreased by galantide ($P<0.05$) but not galanin administration.

We have also shown that administration of galanin or galantide does not influence basal exocrine secretion (volume) in the anaesthetized possum (FIG. 13). Galantide (but not galanin) administration does reduce hyper-stimulated exocrine secretion (FIG. 14).

Example 12

Mouse Pancreatitis Studies

Figure 15:
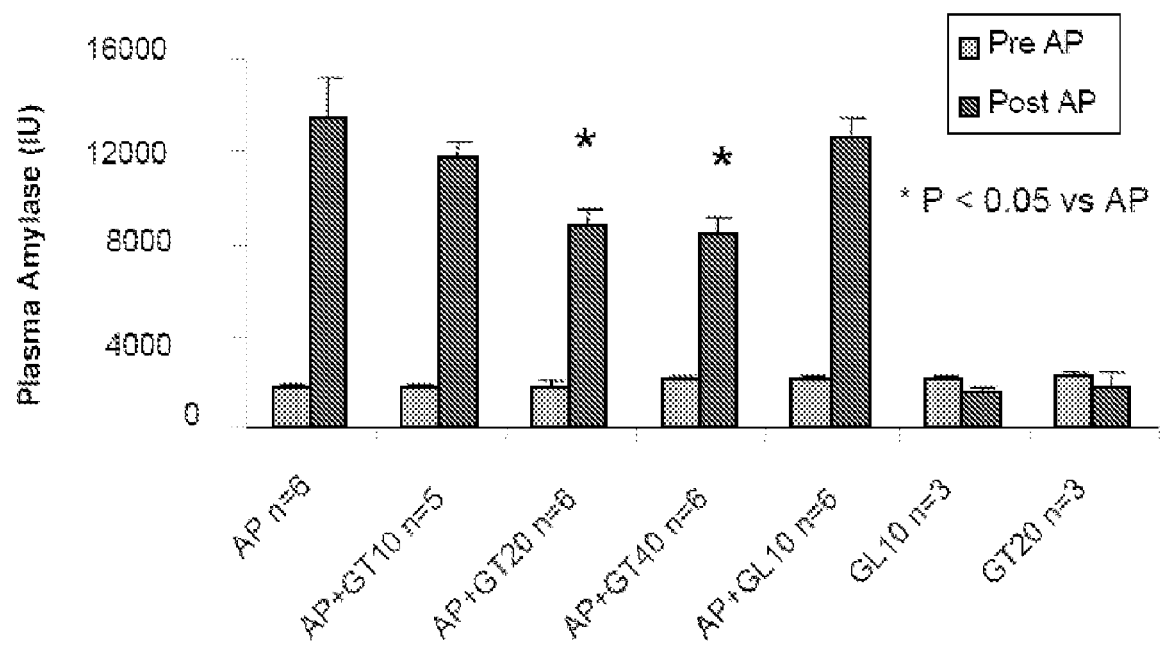
FIG. 15 shows plasma amylase activity in mice with and without acute pancreatitis (AP) induced with caerulein and ±galanin (GL) or galantide (GT) treatment. The induction of AP with 7 hourly i.p. injections of caerulein produced a marked increase in plasma amylase activity. This level was significantly reduced ($P<0.05$) by treatment with GT (20 or 40 nmol/kg) but not with GT (10 nmol/kg) or GL (10 nmol/kg). GT (20 nmol/kg) or GL (10 nmol/kg) did not increase plasma amylase activity above baseline activity.
Figure 16:
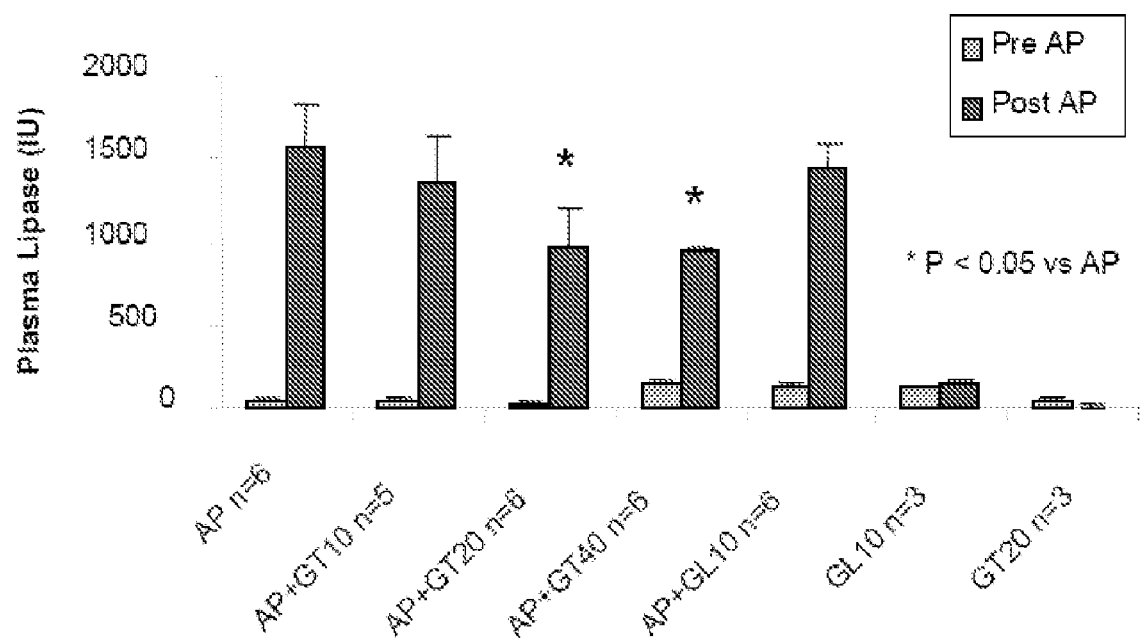
FIG. 16 shows plasma lipase activity from mice with and without acute pancreatitis (AP) induced with caerulein and ±galanin (GL) or galantide (GT) treatment. The induction of AP with 7 hourly i.p. injections of caerulein produced a marked increase in plasma lipase activity. This level was significantly reduced ($P<0.05$) by treatment with GT (20 or 40 nmol/kg) but not with GT (10 nmol/kg) or GL (10 nmol kg). GT (20 nmol/kg) or GL (10 nmol/kg) did not increase plasma lipase activity above baseline activity.
Figure 17:
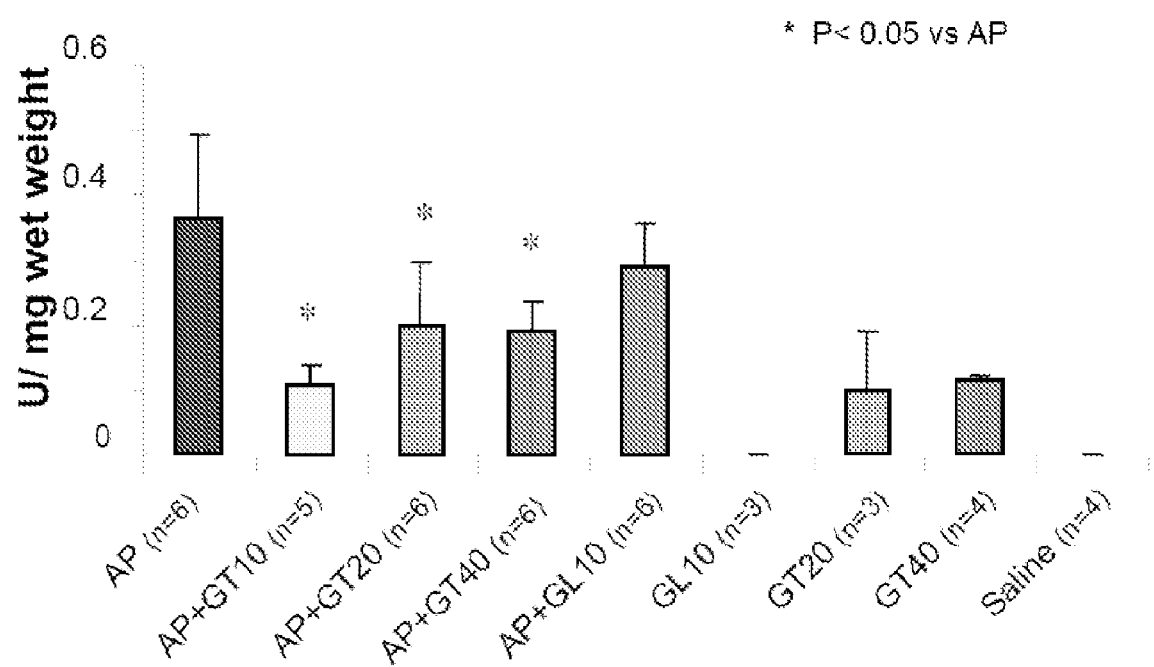
FIG. 17 shows pancreatic myeloperoxidase (MPO) activity from mice with and without acute pancreatitis (AP) induced with caerulein and ±galanin (GL) or galantide (GT) treatment. The induction of AP with 7 hourly i.p. injections of caerulein produced a marked increase in pancreatic MPO activity. This level was significantly reduced ($P<0.05$) by treatment with GT (10, 20 or 40 nmol/kg) but not with GL (10 nmol/kg). GL (10 nmol/kg) alone did not significantly increase pancreatic MPO activity above that measured in saline control. GT (20 or 40 nmol/kg) alone did induce a low level of pancreatic MPO.
Figure 18:
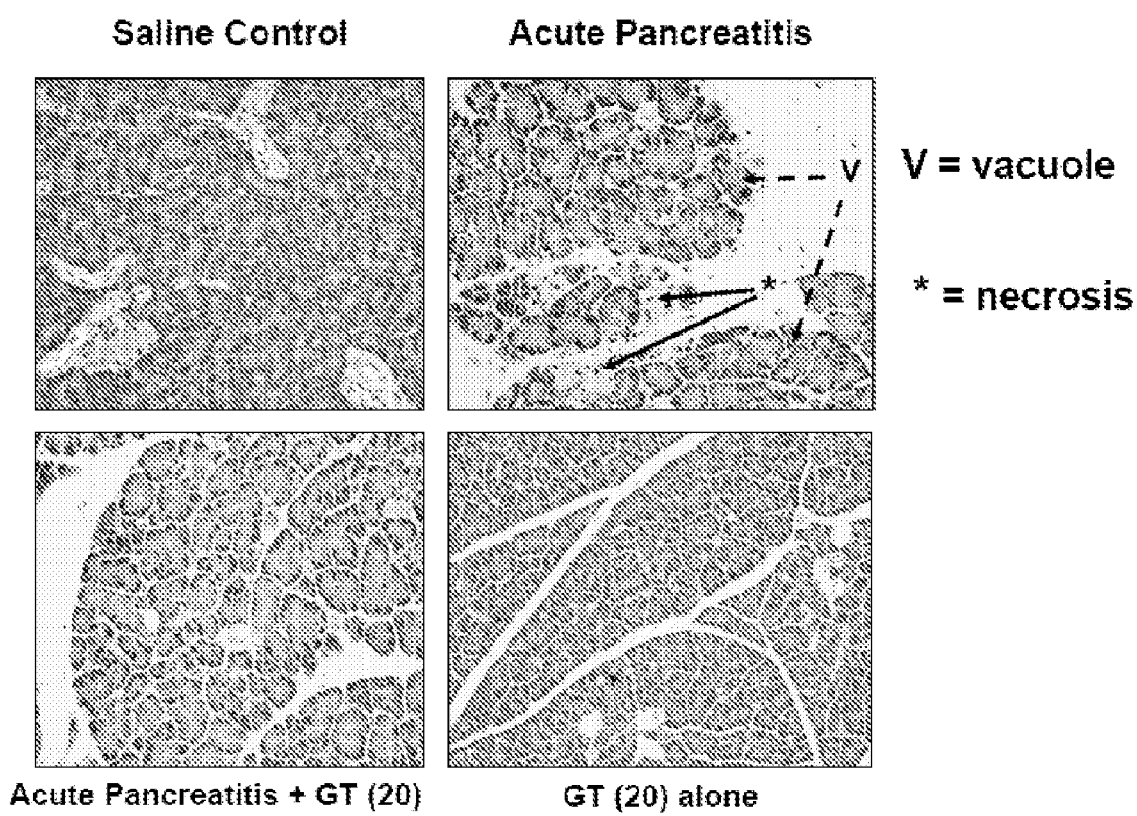
FIG. 18 shows selected images of histological sections illustrating the changes in mouse pancreatic tissue architecture with various treatments. The saline control (top left) illustrates the normal pancreatic architecture. Acute pancreatitis (top right) induces oedema, acinar cell necrosis (*) and vacuolization (V). Acute pancreatitis with galantide (GT; 20 nmol/kg) treatment reduced the acute pancreatitis-induced pancreatic damage (lower left). Mice treated with GT (20 nmol/kg) alone displayed near normal pancreatic architecture (lower right).
Figure 19:
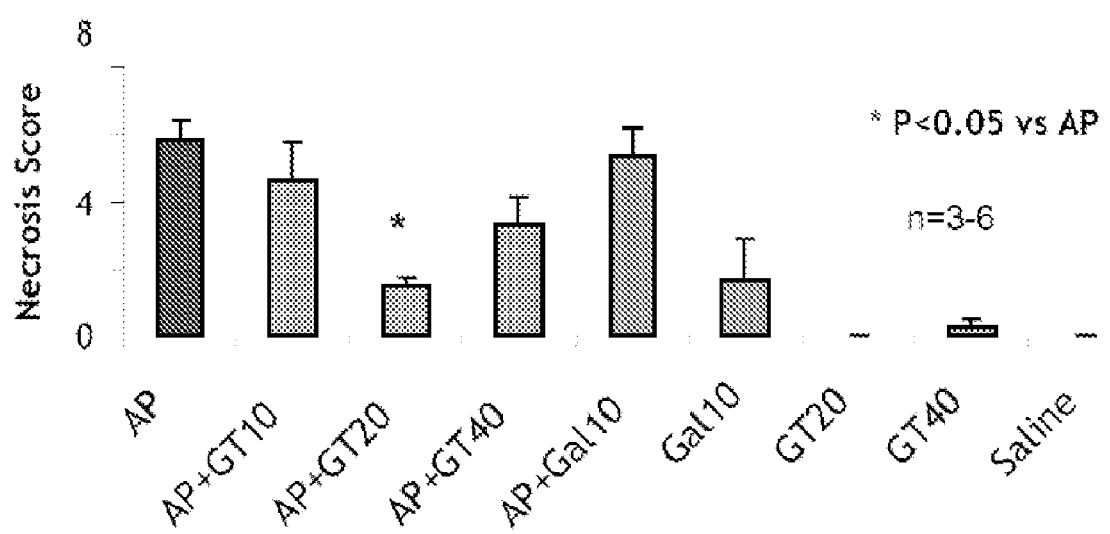
FIG. 19 shows Galantide (GT) treatment reduces the acute pancreatitic (AP)-induced mouse pancreatic acinar cell necrosis. Histological sections from the pancreata of mice used in the studies described in the previous 5 figures were assessed for acinar cell necrosis using a scoring system. GT (20 nmol/kg) significantly reduced the necrosis score (P<0.05). Galanin (GL; 10 nmol/kg) was without effect.
Figure 20:
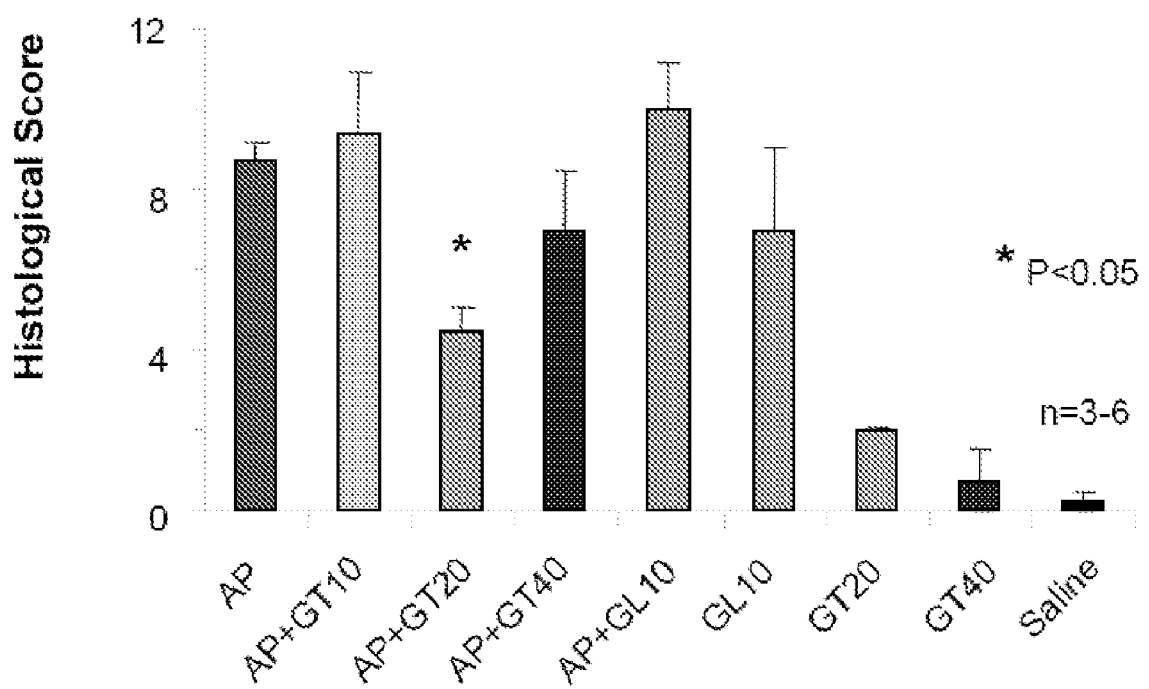
FIG. 20 shows Galantide (GT) treatment reduces the acute pancreatitic (AP)-induced mouse pancreatic damage. Histological sections from the pancreata of mice used in the studies described in the previous 6 figures were assessed for pancreatic tissue damage using a scoring system. GT (20 nmol/kg) significantly reduced the histology score (P<0.05). Galanin (GL; 10 nmol/kg) was without effect.

Comparable studies were performed in a mild (7 caerulein injection) mouse model and the findings are illustrated in FIGS. 15 to 21. FIG. 15 shows the effect on treatment with galanin (GL) or several different doses of galantide (GT) on the pancreatitis-induced plasma amylase levels. Galanin did not alter the plasma amylase level, whereas galantide at 20 and 40 nmol/kg reduced the plasma amylase level. FIG. 16 shows comparable effects on plasma lipase levels. FIG. 17 shows that MPO activity was altered in a similar manner to the plasma enzymes, although the lowest dose of GT was also effective. FIG. 18 presents selected images of histological sections illustrating the changes in pancreatic tissue architecture with various treatments. Quantitative group data of histological changes are presented in FIGS. 19 and 20. Galantide administration (20 nmol/kg) reduced the pancreatitis-induced necrosis whereas galanin had no effect (FIG. 19). A similar change was evident in the histological score, which reflects several parameters (FIG. 20).

In summary, the mouse pancreatitis studies support those in the possum and demonstrate that galantide has the ability to reduce the severity of pancreatitis.

Figure 21A:
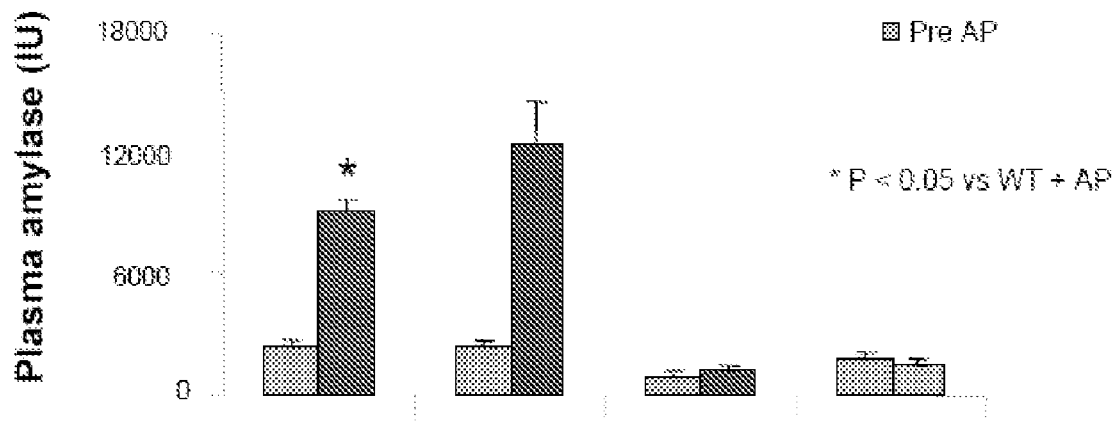
FIG. 21 shows plasma amylase activity from galanin knockout (KO) and wild-type (WT) littermate mice with and without caerulein-induced acute pancreatitis (AP). (A) The elevation in plasma amylase induced for 7 hourly i.p. injections of caerulein in the KO mice was less that that induced in their WT littermates. Plasma amylase activity prior to AP induction is shown. The plasma amylase levels in the KO and WT controls were not elevated above the pre-AP levels. (B) The elevation in plasma lipase induced for 7 hourly i.p. injections of caerulein in the KO mice was less that that induced in their WT littermates (P<0.05). Plasma lipase activity prior to AP induction is shown. The plasma lipase levels in the KO and WT controls were not elevated above the pre-AP levels.
Figure 21B:
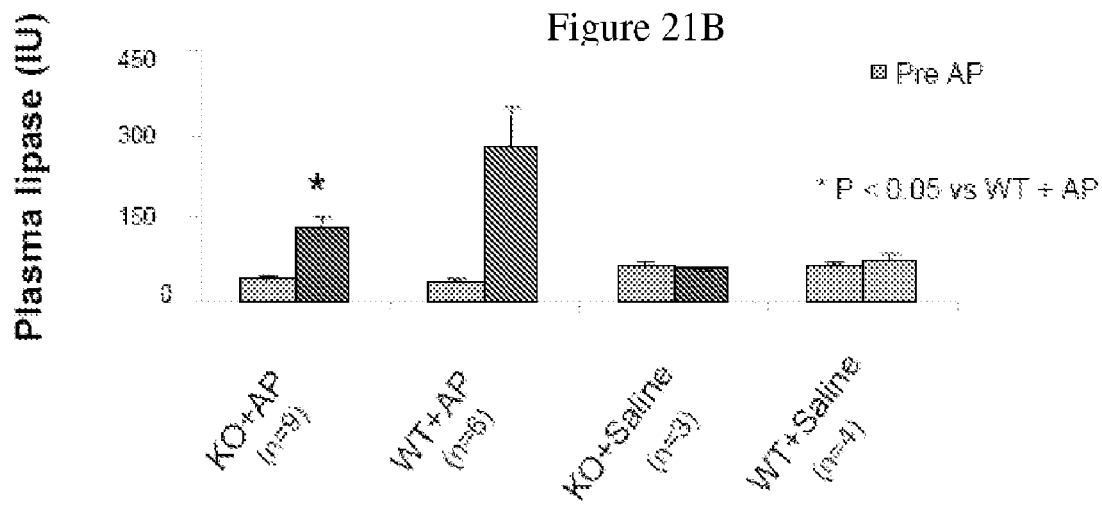
Figure 22:
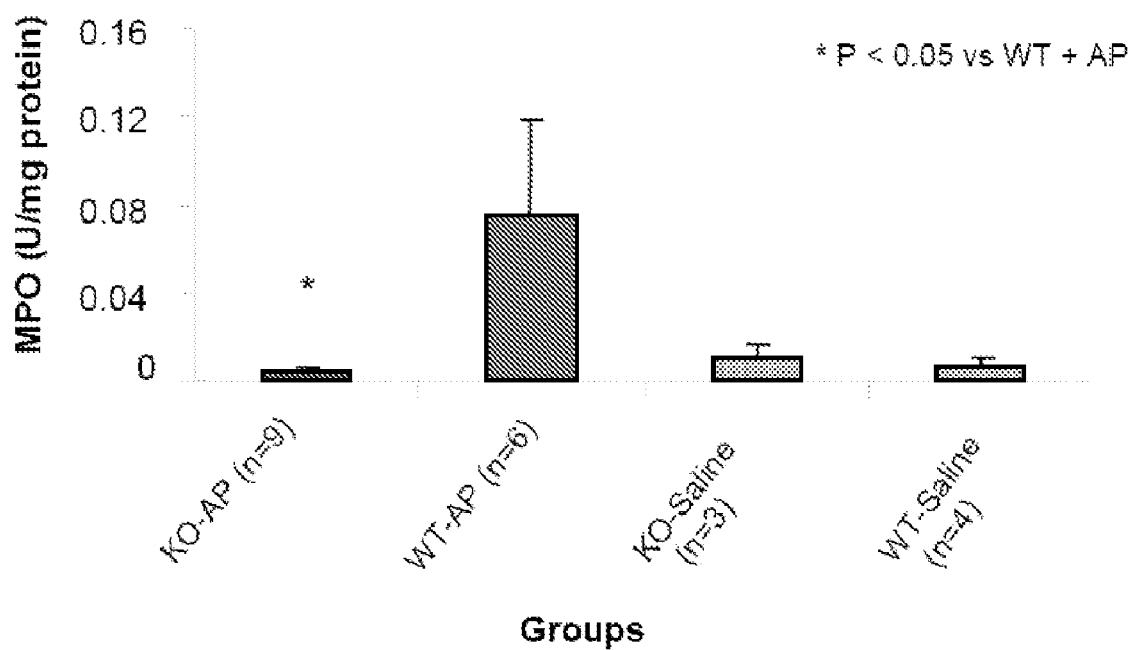
FIG. 22 shows Pancreatic myeloperoxidase (MPO) activity from galanin knockout (KO) and wild-type (WT) littermate mice with and without caerulein-induced acute pancreatitis (AP). The elevation in pancreatic MPO activity induced for 7 hourly i.p. injections of caerulein in the KO mice was markedly less that that induced in their WT littermates (P<0.05). The pancreatic MPO levels in the KO and WT controls were marginally elevated.
Figure 23A:
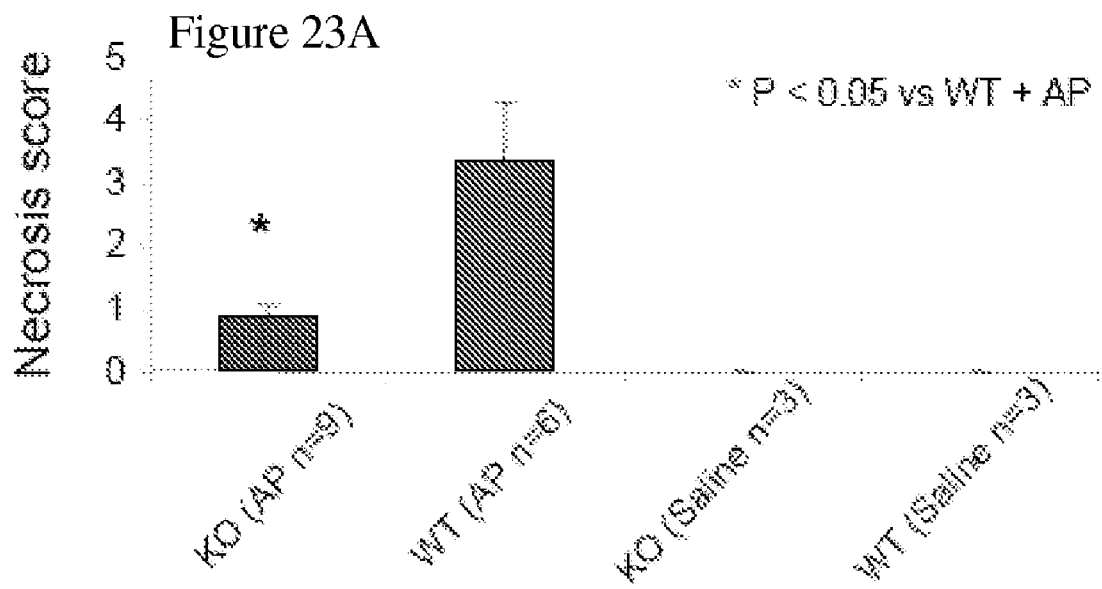
FIG. 23 shows pancreatic acinar cell necrosis from galanin knockout (KO) and wild-type (WT) littermate mice with and without caerulein-induced acute pancreatitis (AP). (A) Histological sections from the pancreata of mice used in the study described in the previous figure were assessed for pancreatic acinar cell necrosis using a scoring system. Necrosis in the pancreas from the KO mice was significantly less than that measured in the WT mice (P<0.05). (B) Histological sections from the pancreata of mice used in the study described in the previous figure were assessed for pancreatic acinar cell vacuolization using a scoring system. Vacuolization in the pancreas from the KO mice was significantly less than that measured in the WT mice (P<0.05).
Figure 23B:
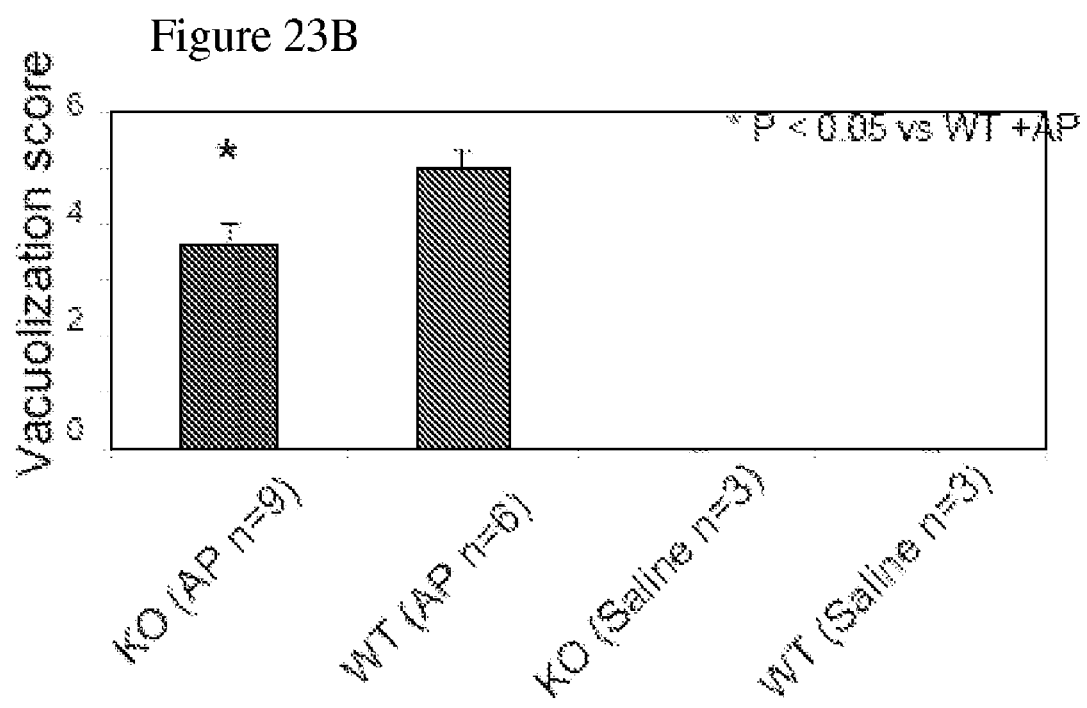
Figure 24A:
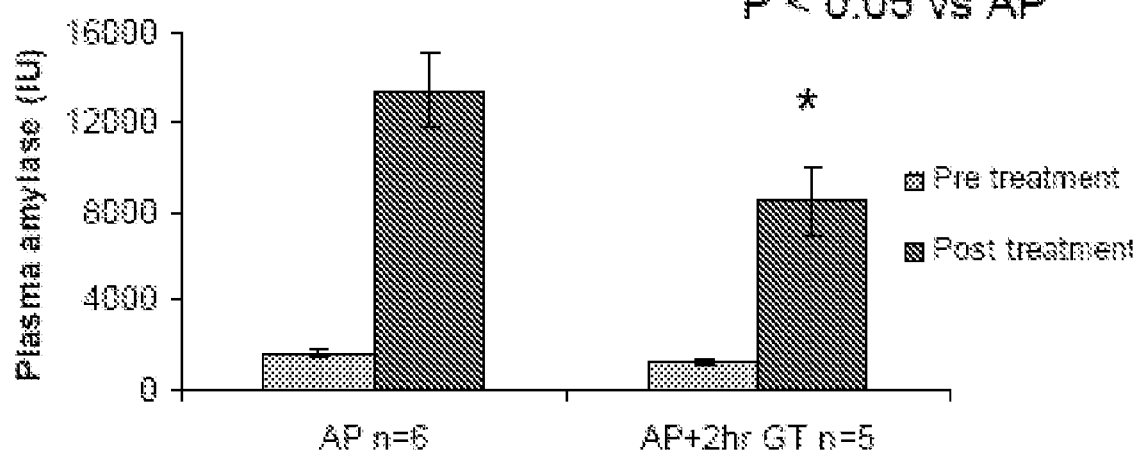
FIG. 24 shows plasma amylase and lipase activity from mice with and without caerulein-induced acute pancreatitis (AP)±galantide (GT) treatment delayed for 2 hours post-AP induction. (A) The elevation in plasma amylase induced for 7 hourly i.p. injections of caerulein was significantly reduced by the delayed treatment with GT (40 nmol/kg). Plasma amylase activity prior to AP induction (pre treatment) is shown. (B) The elevation in plasma lipase induced for 7 hourly i.p. injections of caerulein was significantly reduced by the delayed treatment with GT (40 nmol/kg). Plasma lipase activity prior to AP induction (pre treatment) is shown.
Figure 24B:
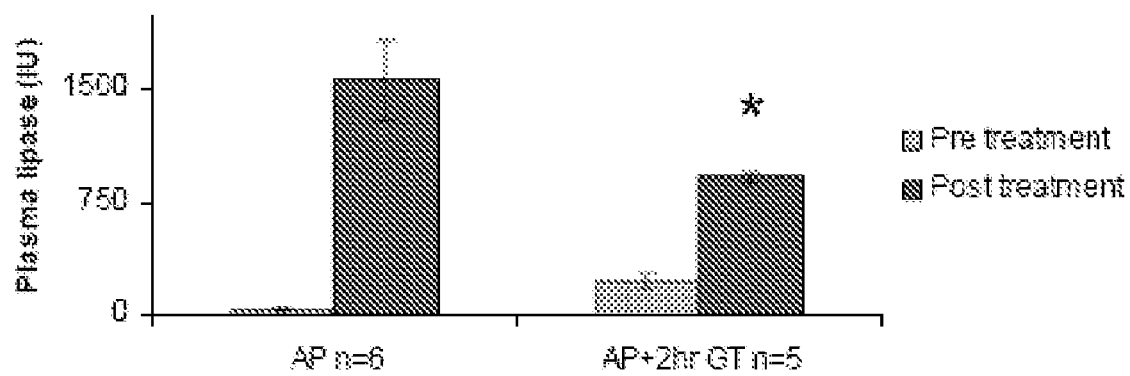

To provide further support for the concept that galanin pays a major role in the onset and progression of acute pancreatitis (AP), studies with galanin knock mice were undertaken. Using the 7 injection caerulein protocol, the pancreatitis-induced plasma hyperenzymemia was reduced in the galanin knock mice (KO) compared with that produced in the wild type (WT) littermates (FIG. 21). A more dramatic decrease was evident in the level of acute pancreatitis-induce pancreatic MPO activity (FIG. 22). Similar changes were evident in the level of pancreatic necrosis and vacuolization in the knock out mice compare with wild type littermates (FIG. 23). We have recently undertaken a comparable study in which the galantide is administered to knock out and wild type mice 2 hours post pancreatitis onset. Preliminary results (FIG. 24) show that delayed galantide treatment reduces the pancreatitis-induced plasma hyperenzymemia compare to wild type littermates.

In summary, these data show that the galanin knock out mice are less susceptible to pancreatitis that their wild type littermates and provides further supports for role of galanin in the onset and progression of acute pancreatitis.

Figure 25:
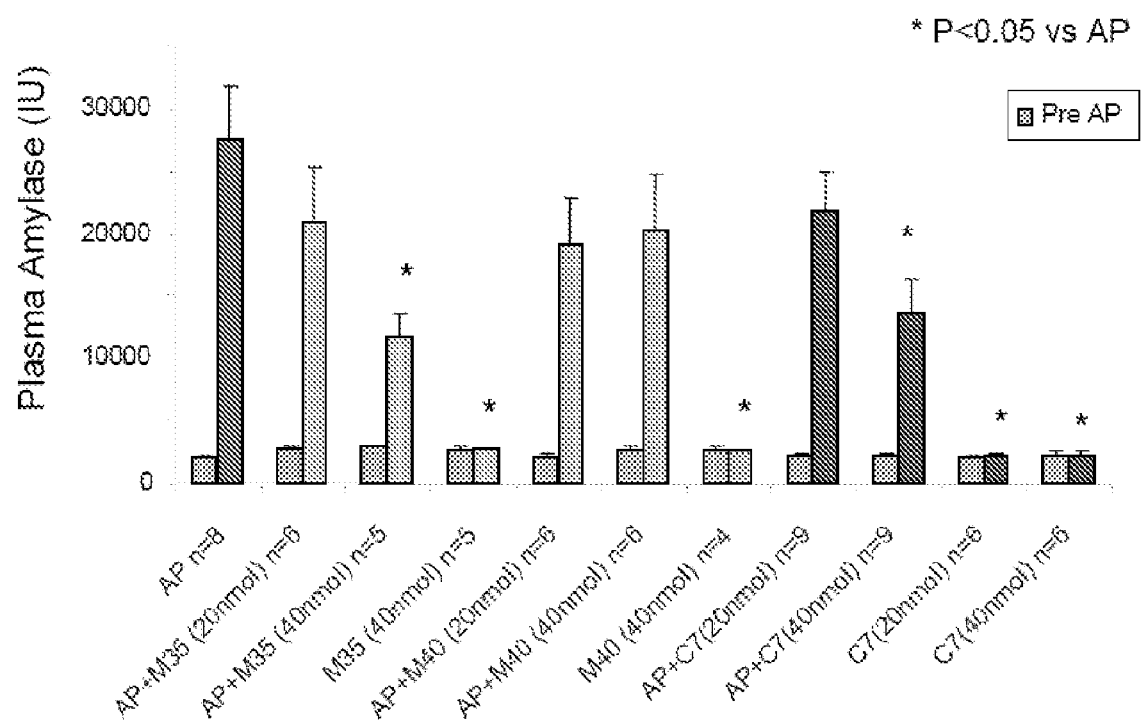
FIG. 25 shows plasma amylase activity from mice with and without caerulein-induced acute pancreatitis (AP)±treatment with the galanin antagonists M35, M40 and C7. The induction of AP with 7 hourly i.p. injections of caerulein produced a marked increase in plasma amylase activity relative to the pre AP activity. This level was significantly reduced (P<0.05) by treatment with M35 (40 nmol/kg) and C7 (40 nmol/kg) but not with M40. Treatment with the antagonists alone did not increase plasma amylase activity above pre AP activity.
Figure 26:
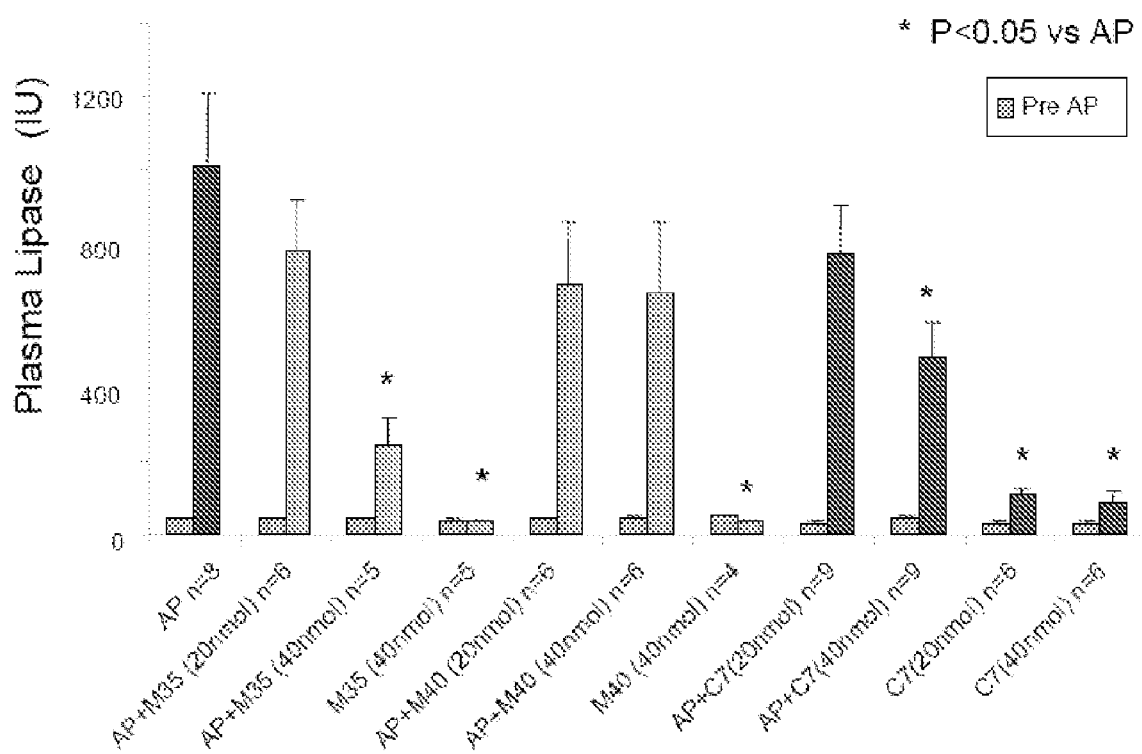
FIG. 26 shows plasma lipase activity from mice with and without caerulein-induced acute pancreatitis (AP)±treatment with the galanin antagonists M35, M40 and C7. The induction of AP with 7 hourly i.p. injections of caerulein produced a marked increase in plasma lipase activity relative to the pre AP activity. This level was significantly reduced (P<0.05) by treatment with M35 (40 nmol/kg) and C7 (40 nmol/kg) but not with M40. Treatment with the antagonists alone did not increase plasma lipase activity above pre AP activity.
Figure 27:
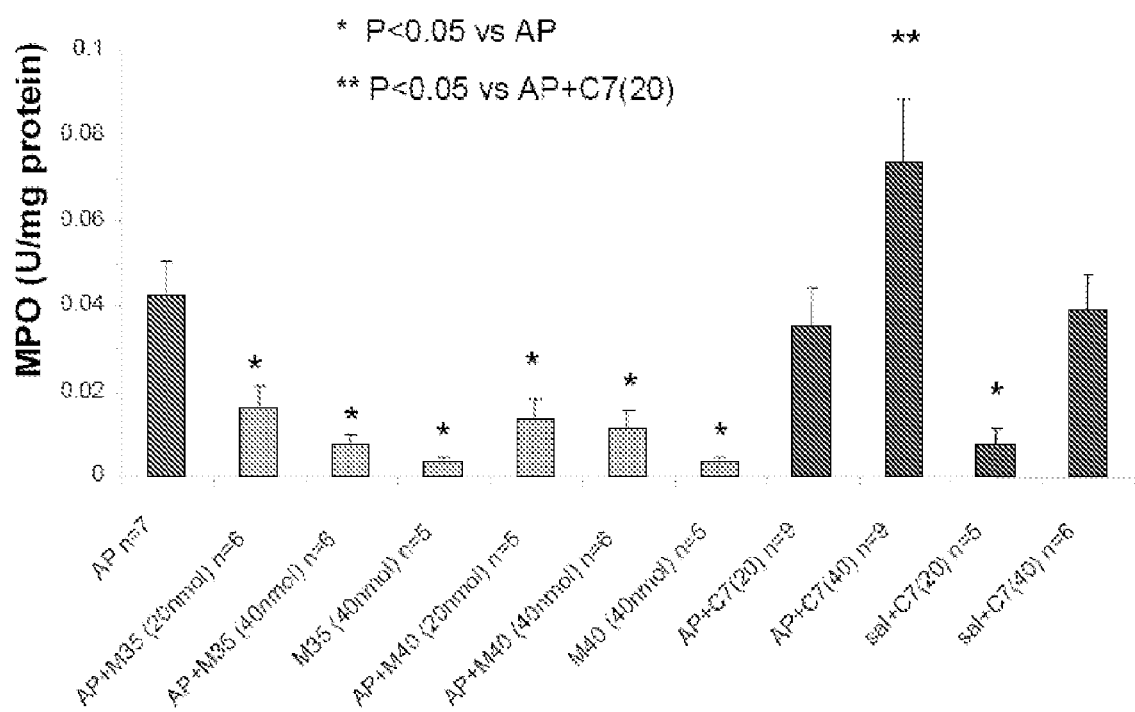
FIG. 27 shows pancreatic myeloperoxidase (MPO) activity from mice with and without caerulein-induced acute pancreatitis (AP)±treatment with the galanin antagonists M35, M40 and C7. The induction of AP with 7 hourly i.p. injections of caerulein produced a marked increase in pancreatic MPO activity. This level was significantly reduced (P<0.05) by treatment with M35 and M40 (20 and 40 nmol/kg). In contrast, C7 (40 nmol/kg) treatment increased the pancreatic MPO activity above that seen with AP alone. Moreover, C7 (40 nmol/kg) administered alone significantly elevated pancreatic MPO activity
Figure 28:
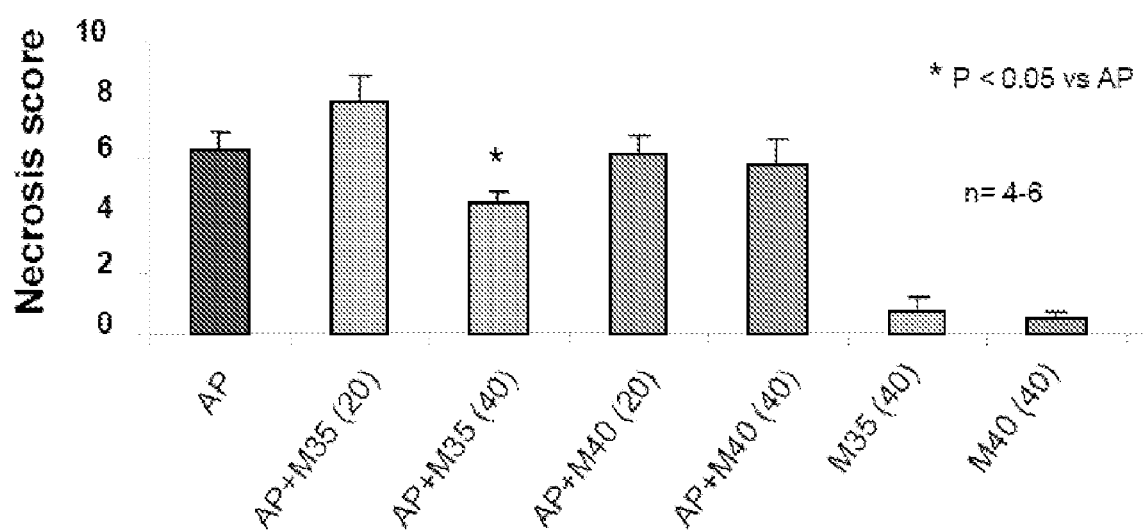
FIG. 28 shows pancreatic acinar cell necrosis from mice with and without caerulein-induced acute pancreatitis (AP) ±treatment with the galanin antagonists M35 and M40. Histological sections from the pancreata of mice used in the study described in the previous figure were assessed for pancreatic acinar cell necrosis using a scoring system. AP-induced pancreatic acinar cell necrosis from mice treated with M35 (40 nmol/kg) was significantly reduced (P<0.05). Treatment with M40 was without effect.
Figure 29:
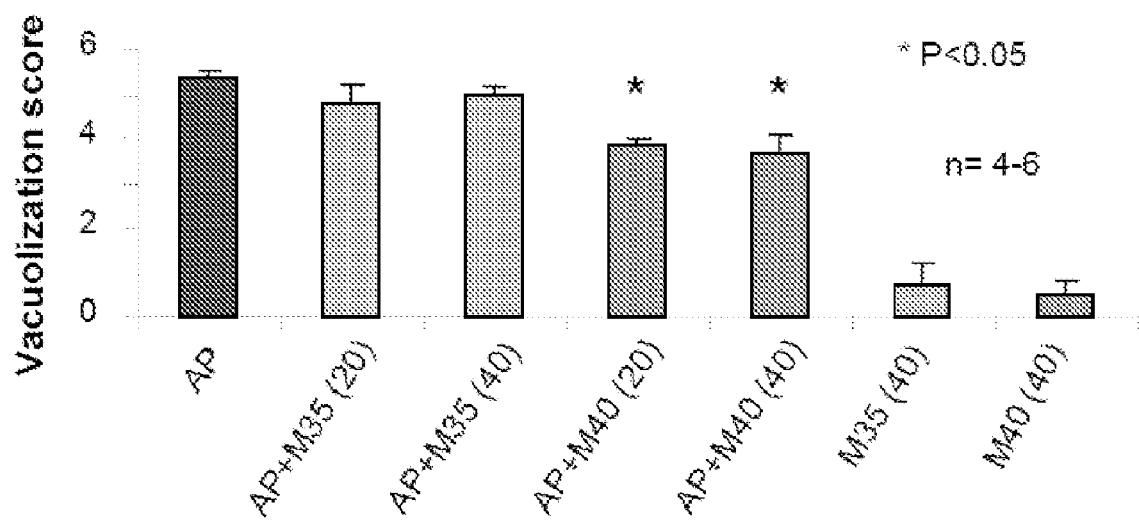
FIG. 29 shows pancreatic acinar cell vacuolization from mice with and without caerulein-induced acute pancreatitis (AP)±treatment with the galanin antagonists M35 and M40. Histological sections from the pancreata of mice used in the study described in the previous figure were assessed for pancreatic acinar cell vacuolization using a scoring system. AP-induced pancreatic acinar cell vacuolization from mice treated with M40 (20 and 40 nmol/kg) was significantly reduced (P<0.05). Treatment with M35 was without effect.

Further studies were undertaken in the mouse models to explore the efficacy of other available galanin antagonists. Two doses of M35, M40 or C7 were evaluated using the 7 injection caerulein mouse model. These data are summarized in FIGS. 25 to 29. FIG. 25 shows that the elevated plasma amylase activity induced by acute pancreatitis is depressed by the 40 nmol/kg dose of M35 and C7, but not M40. Comparable changes were noted with plasma lipase activity (FIG. 26). Pancreatic MPO activity induced by acute pancreatitis was decreased by M35 and M40, but not by C7 (FIG. 27). In fact the highest dose of C7 increased the level of acute pancreatitis-induced MPO activity and even when administered alone produced an increase in pancreatic MPO activity. To date the pancreatic necrosis and vacuolization has been quantified for M35 and M40 treatment groups and the data is shown in FIGS. 28 and 29. The high dose of M35 but not M40 reduced the necrosis score (FIG. 28) which is in keeping with the actions of these two antagonists on plasma hyperenzymemia (FIGS. 25 & 26). Interestingly, M35 failed to improve the acute pancreatitic-induced vacuolization, whereas M40 did (FIG. 29).

In summary some of the other galanin antagonists have beneficial properties similar to galantide, but the effects are complex. For example M40's failure to reduce the pancreatitis-induced plasma hyperenzymemia may reflect a suboptimal dose rather that different receptor selectivity.

Future studies will evaluate more selective galanin antagonists (e.g. M871 for selective for GalR2—Sollenberg et al. (2006) *International Journal of Peptide Research and Therapeutics* 12(2): 115-119 and the possible involvement of somatostatin by evaluation of somatostatin specific antagonists. Galanin receptor knock out mice will also be investigated as these become available.

Finally, it will be appreciated that various modifications and variations of the methods and compositions of the invention described herein will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are apparent to those skilled in the art are intended to be within the scope of the present invention.

The invention claimed is:

1. A method for the prevention and/or treatment of pancreatitis in a human subject, the method comprising administering to the subject a therapeutically effective amount of a Galanin antagonist and/or a Galanin receptor antagonist, wherein the human subject is susceptible to or in need of treatment for pancreatitis.

2. A method according to claim 1, wherein the pancreatitis is acute pancreatitis.

3. A method according to claim 1, wherein the Galanin antagonist and/or Galanin receptor antagonist is administered to the subject at one of prior to the onset of the pancreatitis, concurrently with the onset of the pancreatitis, or in the early phase of the pancreatitis.

4. A method according to claim 3, wherein the administration of the Galanin antagonist and/or Galanin receptor antagonist during the early phase of pancreatitis is administration within 24 hours of the onset of the pancreatitis.

5. A method according to claim 1, wherein the Galanin antagonist is Galantide, or a functional variant, analogue, derivative, or fragment thereof.

6. A method according to claim 5, wherein a dose of Galantide administered to the subject is in the range from 0.1 nmol/kg to 100 nmol/kg.

7. A method according to claim 1 wherein the treatment of pancreatitis comprises an improvement in pancreatic vascular perfusion.

8. A method according to claim 1 wherein the treatment of pancreatitis comprises reducing pancreatic inflammation.

9. A method according to claim 1 wherein the treatment of pancreatitis comprises reducing pancreatic damage due to inflammation of the pancreas.

10. A method according to claim 1 wherein the prevention and/or treatment of pancreatitis comprises inhibiting the progression of acute pancreatitis.

11. A method according to claim 1, wherein the method further comprises administering to the subject a therapeutically effective amount of one or more agents selected from the group consisting of an analgesic, including a non-narcotic and an opiate narcotic; an antibiotic; an agent that suppresses production of pancreatic enzymes, including somatostatin, octreotide, aprotinin, and gabexate mesilate; an agent that suppresses stomach acid, including H2-receptor blockers and proton pump inhibitors; a pancreatic enzyme supplement; a steroid; a dehydrating fluid; an endothelin antagonist; insulin; an agent that interferes with ICAM; a B2-Bradykinin inhibitor; a Kallikrein inhibitor; a protease activated receptor antagonist; Met RANTES; an angiotension II receptor antagonist, including candesartan; a MCP-1 synthesis blocker, including bindarit; a nitric oxide donor; a nitric oxide synthase inhibitor, including an inducible nitric oxide synthase inhibitor; an anti-ulcer agent; an ionotope; factor VII; activated protein C; calcium; glucose; a blood product including plasma and/or platelets; and butamene.

12. A method according to claim 1, wherein the method comprises administering to the subject a therapeutically effective amount of (i) somatostatin, or a functional variant, analogue, derivative or fragment thereof; and (ii) a Galanin antagonist and/or a Galanin receptor antagonist.

13. A composition method according to claim 1, wherein the method comprises treating a subject suffering from pancreatitis.

14. A method according to claim 1, wherein the method comprises preventing pancreatitis in a subject susceptible to acute pancreatitis.

15. A method according to claim 14, wherein the acute pancreatitis is due to a medical procedure, damage to the pancreas from surgery or endoscopy, damage to the pancreas from blunt or penetrating injuries, drug use, hereditary pancreatitis, a gallstone, alcohol abuse, hyperlipidemia, estrogen use associated with high lipid levels, hyperparathyroidism, a high level of calcium in the blood, reduced blood supply to the pancreas, Mumps, pancreatic cancer, and kidney transplantation.

* * * * *